(12) United States Patent
Pollock et al.

(10) Patent No.: US 8,703,744 B2
(45) Date of Patent: Apr. 22, 2014

(54) CHOLESTEROL LEVEL LOWERING LIPOSOMES

(75) Inventors: Stephanie Pollock, Oxford (GB); Raymond Dwek, Oxford (GB); Nicole Zitzmann, Oxford (GB)

(73) Assignee: The Chancellor, Masters and Scholars of the University of Oxford, Oxford (GB)

( * ) Notice: Subject to any disclaimer, the term of this patent is extended or adjusted under 35 U.S.C. 154(b) by 763 days.

(21) Appl. No.: 12/732,630

(22) Filed: Mar. 26, 2010

(65) Prior Publication Data

US 2010/0266678 A1  Oct. 21, 2010

Related U.S. Application Data

(60) Provisional application No. 61/202,699, filed on Mar. 27, 2009.

(51) Int. Cl.
 *A61K 9/127* (2006.01)
 *A61P 31/12* (2006.01)

(52) U.S. Cl.
 USPC .......................... 514/76; 424/450

(58) Field of Classification Search
 None
 See application file for complete search history.

(56) References Cited

U.S. PATENT DOCUMENTS

| | | |
|---|---|---|
| 4,246,345 A | 1/1981 | Kinast et al. |
| 4,266,025 A | 5/1981 | Kinast et al. |
| 4,405,714 A | 9/1983 | Kinast et al. |
| 4,639,436 A | 1/1987 | Junge et al. |
| 4,792,558 A | 12/1988 | Sunkara et al. |
| 4,806,650 A | 2/1989 | Schroeder et al. |
| 4,837,237 A | 6/1989 | Rohrschneider et al. |
| 4,849,430 A | 7/1989 | Fleet et al. |
| 4,861,892 A | 8/1989 | Fleet |
| 4,876,268 A | 10/1989 | Koszyk et al. |
| 4,894,388 A | 1/1990 | Fleet |
| 4,904,769 A | 2/1990 | Rauenbusch |
| 4,910,310 A | 3/1990 | Campbell et al. |
| 4,925,796 A | 5/1990 | Bergh et al. |
| 4,952,585 A | 8/1990 | Sunkara et al. |

(Continued)

FOREIGN PATENT DOCUMENTS

| | | |
|---|---|---|
| AU | 5310773 A | 9/1974 |
| DE | 196 23 950 A1 | 12/1997 |

(Continued)

OTHER PUBLICATIONS

Sharookh B. Kapadia, Heidi Barth, Thomas Baumert, Jane A. McKeating, and Francis V. Chisari. Initiation of Hepatitis C Virus Infection Is Dependent on Cholesterol and Cooperativity between CD81 and Scavenger Receptor B Type I. Journal of Virology, vol. 81, No. 1, Jan. 2007, p. 374-383.*

(Continued)

*Primary Examiner* — Brian Gulledge
*Assistant Examiner* — Michael P Cohen
(74) *Attorney, Agent, or Firm* — Foley & Lardner LLP

(57) ABSTRACT

Provided are methods of reducing cellular cholesterol levels using lipid particles that are capable of cellular entry. Such lipid particles may be used for treating or preventing a disease or condition that is caused by or associated with an increased cellular cholesterol level and for treating or preventing a disease or condition, that is caused by or associated with a virus, that relies on cellular cholesterol for its replication.

14 Claims, 11 Drawing Sheets

(56) References Cited

U.S. PATENT DOCUMENTS

| | | | |
|---|---|---|---|
| 4,994,572 | A | 2/1991 | Fleet |
| 4,996,329 | A | 2/1991 | Fleet et al. |
| 5,004,746 | A | 4/1991 | Liu et al. |
| 5,011,929 | A | 4/1991 | Fleet et al. |
| 5,013,842 | A | 5/1991 | Fleet et al. |
| 5,017,704 | A | 5/1991 | Fleet et al. |
| 5,043,273 | A | 8/1991 | Scudder et al. |
| 5,100,797 | A | 3/1992 | Fleet et al. |
| 5,200,523 | A | 4/1993 | Fleet |
| 5,214,050 | A | 5/1993 | Bitonti et al. |
| 5,229,376 | A | 7/1993 | Alving et al. |
| 5,264,356 | A | 11/1993 | Rohrschneider |
| 5,286,877 | A | 2/1994 | Behling et al. |
| 5,385,911 | A | 1/1995 | Sunkara et al. |
| 5,401,645 | A | 3/1995 | Grabner et al. |
| 5,411,970 | A | 5/1995 | Partis et al. |
| 5,472,969 | A | 12/1995 | Platt et al. |
| 5,573,779 | A | 11/1996 | Sato et al. |
| 5,580,884 | A | 12/1996 | Platt et al. |
| 5,591,448 | A | 1/1997 | Tepic |
| 5,622,972 | A | 4/1997 | Bryant et al. |
| 5,643,888 | A | 7/1997 | Rohrschneider |
| 5,691,346 | A | 11/1997 | Willenborg et al. |
| 5,709,865 | A | 1/1998 | Van den Hurk et al. |
| 5,750,648 | A | 5/1998 | Chang et al. |
| 5,837,709 | A | 11/1998 | Willenborg et al. |
| 5,908,867 | A | 6/1999 | Henry et al. |
| 5,911,989 | A | 6/1999 | Katinger et al. |
| 6,041,252 | A | 3/2000 | Walker et al. |
| 6,136,820 | A | 10/2000 | Liu et al. |
| 6,172,046 | B1 | 1/2001 | Albrecht et al. |
| 6,177,074 | B1 | 1/2001 | Glue et al. |
| 6,225,325 | B1 | 5/2001 | Jacob |
| 6,299,872 | B1 | 10/2001 | Albrecht et al. |
| 6,387,365 | B1 | 5/2002 | Albrecht et al. |
| 6,465,487 | B1 | 10/2002 | Block et al. |
| 6,465,488 | B1 | 10/2002 | Butters et al. |
| 6,472,373 | B1 | 10/2002 | Albrecht |
| 6,515,028 | B1 | 2/2003 | Mueller et al. |
| 6,524,570 | B1 | 2/2003 | Glue et al. |
| 6,545,021 | B1 | 4/2003 | Mueller et al. |
| 6,583,158 | B1 | 6/2003 | Fan et al. |
| 6,589,964 | B2 | 7/2003 | Fan et al. |
| 6,599,919 | B2 | 7/2003 | Fan et al. |
| 6,656,912 | B2 | 12/2003 | Perlmutter et al. |
| 6,689,759 | B1 | 2/2004 | Jacob et al. |
| 6,809,083 | B1 | 10/2004 | Mueller et al. |
| 6,824,768 | B2 | 11/2004 | Stalgis et al. |
| 6,916,829 | B2 | 7/2005 | Fan et al. |
| 7,141,582 | B2 | 11/2006 | Fan et al. |
| 2002/0006909 | A1 | 1/2002 | Perlmutter et al. |
| 2002/0151683 | A1 | 10/2002 | Kim et al. |
| 2002/0188011 | A1 | 12/2002 | King et al. |
| 2003/0124160 | A1 | 7/2003 | Petrescu et al. |
| 2003/0124181 | A1 | 7/2003 | Tardi et al. |
| 2003/0158122 | A1 | 8/2003 | Sparks |
| 2004/0009126 | A1 | 1/2004 | Pilkiewicz et al. |
| 2004/0110795 | A1 | 6/2004 | Zitzmann et al. |
| 2004/0224011 | A1* | 11/2004 | Rodrigueza et al. ......... 424/450 |
| 2005/0013855 | A1* | 1/2005 | Gould-Fogerite et al. .... 424/450 |
| 2005/0053625 | A1 | 3/2005 | Block et al. |
| 2006/0093577 | A1 | 5/2006 | Dugourd |
| 2006/0194835 | A1 | 8/2006 | Dugourd et al. |
| 2007/0275998 | A1 | 11/2007 | Butters et al. |
| 2008/0131398 | A1 | 6/2008 | Jeffs et al. |
| 2008/0138351 | A1* | 6/2008 | Dwek et al. ................ 424/148.1 |
| 2009/0252785 | A1 | 10/2009 | Pollock et al. |
| 2011/0182982 | A1 | 7/2011 | Dwek et al. |

FOREIGN PATENT DOCUMENTS

| | | |
|---|---|---|
| EP | 1 829 526 A1 | 9/2007 |
| FR | 2 221 122 A1 | 10/1974 |
| WO | WO 90/11781 A1 | 10/1990 |
| WO | WO 98/33520 A1 | 8/1998 |
| WO | WO 99/24401 A1 | 5/1999 |
| WO | WO 01/10429 A2 | 2/2001 |
| WO | WO 01/54692 A1 | 8/2001 |
| WO | WO 02/24162 A1 | 3/2002 |
| WO | WO 03/024422 A1 | 3/2003 |
| WO | WO 03/032946 A2 | 4/2003 |
| WO | WO 03/037265 A2 | 5/2003 |
| WO | WO 2005/063213 A1 | 7/2005 |
| WO | WO 2006/049307 A1 | 5/2006 |
| WO | WO 2007/127439 A2 | 11/2007 |
| WO | WO 2009/011007 A2 | 1/2009 |

OTHER PUBLICATIONS

Chang et al., "pH-Sensitive Liposomes as Adjuvants for Peptide Antigens," Methods in Enzymology, 2003, 373:127-136.

Weber et al., "Granulocyte-Macrophage-Colony-Stimulating Factor Added to a Multipeptide Vaccine for Resected Stage II Melanoma," Cancer, Jan. 1, 2003, 97(1):186-200.

Aiello et al., "Increased Atherosclerosis in Hyperlipidemic Mice with Inactivation of ABCA21 in Macrophages," Arterioscler Thromb Vasc Biol., 2002, 22(4): 630-637.

Aizaki et al., "Characterization of the hepatitis C virus RNA replication complex associated with lipid rafts," Virology, 2004, 324(2): 450-461.

Aizaki et al., "Critical Role of Virion-Associated Cholesterol and Sphingolipid in Hepatitis C Virus Infection," J Virol., 2008, 82(12): 5715-5724.

Alfano et al., "The B-Oligomer of Pertussis Toxin Deactivates CC Chemokine Receptor 5 and Blocks Entry of M-tropic HIV-1 strains," J Exp Med., 1999, 190(5): 597-606.

U.S. Appl. No. 12/656,992, filed Feb. 22, 2010, Ramstedt et al.

U.S. Appl. No. 12/656,993, filed Feb. 22, 2010, Ramstedt et al.

Allred et al., "Estrogen receptor-alpha mediates gender differences in atherosclerosis in duced by HIV protease inhibitors," J Biol Chem., 2006, 281(3): 1419-1425.

Aloia et al., "Lipid composition and fluidity of the human immunodeficiency virus envelope and host cell plasma membranes," Proc Natl Acad Sci U S A, 1993, 90(11): 5181-5185.

Babitt et al., "Murine SR-BI, a High Density Lipoprotein Receptor that Mediates Selective Lipid Uptake, is N-Glycosylated and Fatty Acylated and Colocalizes with Plasma Membrane Caveolae," J Biol Chem., 1997, 272(20): 13242-13249.

Bavari et al., "Lipid Raft Microdomains: A Gateway for Compartmentalized Trafficking of Ebola and Marburg Viruses," J Exp Med., 2002, 195(5): 593-602.

Beer et al., "Amphotropic murine leukaemia virus envelope protein is associated with cholesterol-rich microdomains," Virol J., 2005, 2(1): 36.

Bergeron et al., "Calnexin: a membrane-bound chaperone of the endoplasmic reticulum," TIBS, Mar. 19, 1994, pp. 124-128.

Block et al., "Treatment of chronic hepadnavirus infection in a woodchuck animal model with an inhibitor of protein folding and trafficking," Nature Medicine, May 1998, 4(5):610-614.

Blum et al., "Antiviral therapy of hepatitis B virus infection: Blocking viral gene expression," Advanced Drug Delivery Reviews, 1995, 17:321-331.

Branza-Nichita et al., "Antiviral Effect of N-Butyldeoxynojirimycin against Bovine Viral Diarrhea Virus Correlates with Misfolding of E2 Envelope Proteins and Impairment of Their Association into E1-E2 Heterodimers," Journal of Virology, Apr. 2001, 75(8):3527-3536.

Bremer et al., "Hepatitis B virus infection is dependent on cholesterol in the viral envelope," Cellular Microbiology, 2009, 11(2): 249-260.

Brown et al., "A proteolytic pathway that controls the cholesterol content of membranes, cells, and blood," Proc Natl Acad Sci U S A, 1999, 96(20): 11041-11048.

Buhaescu et al., "Mevalonate pathway: A review of clinical and therapeutical implications," Clin Biochem., 2007, 40(9-10): 575-584.

Campbell et al., "Lipid rafts and HIV-1: from viral entry to assembly of progeny virions," J Clin Virol., 2001, 22(3): 217-227.

(56) References Cited

OTHER PUBLICATIONS

Campbell et al., "Virion-associated cholesterol is critical for the maintenance of HIV-1 structure and infectivity," AIDS, 2002, 16(17): 2253-2261.
Carpentier et al., "Mechanism of highly active anti-retroviral therapy-induced hyperlipidemia in HIV-infected individuals," Atherosclerosis, 2005, 178(1): 165-172.
Charrin et al., "A physical and functional link between cholesterol and tetraspanins," Eur J Immunol., 2003, 33(9): 2479-2489.
Chatterjee et al., "Novel Mutations that Control the Sphingolipid and Cholesterol Dependence of the Semliki Forest Virus Fusion Protein," J Virol., 2002, 76(24): 12712-12722.
Cherukuri et al., "The Tetraspanin CD81 Is Necessary for Partitioning of Coligated CD19/CD21-B Cell Antigen Receptor Complexes into Signaling-Active Lipid Rafts," J Immunol., 2004, 172(1): 370-380.
Chisari, F. V., "Unscrambling hepatitis C virus-host interactions," Nature, 2005, 436(7053): 930-932.
Chung et al., "Vaccinia Virus Penetration Requires Cholesterol and Results in Specific Viral Envelope Proteins Associated with Lipid Rafts," J Virol., 2005, 79(3): 1623-1634.
del Real et al., "Statins Inhibit HIV-1 Infection by Down-regulating Rho Activity," J Exp Med., 2004, 200(4): 541-547.
Dhaliwal et al., "Cholesterol delivered to macrophages by oxidized low density lipoprotein is sequestered in lysosomes and fails to efflux normally," J Lipid Res., 2000, 41(10): 1658-1665.
Dibisceglie et al., "Optimal Therapy of Hepatitis C," Hepatology, Nov. 2002, S121-S127.
Ding et al., "Independent Segregation of Human Immunodeficiency Virus Type 1 Gag Protein Complexes and Lipid Rafts," J Virol., 2003, 77(3): 1916-1926.
Durantel et al., "Study of the Mechanism of Antiviral Action of Iminosugar Derivatives against Bovine Viral Diarrhea Virus," Journal of Virology, Oct. 2001, 75(19):8987-8998.
Dwek et al., "Targeting glycosylation as a therapeutic approach," Nature Reviews, Drug Discovery, Jan. 2002, 1:65-75.
El-Sadr et al., "Effects of HIV disease on lipid, glucose and insulin levels: resulst from a large antiretroviral-naive cohort," HIV Med., 2005, 6(2): 114-121.
Empig et al., "Association of the Caveola Vesicular System with Cellular Entry by Filoviruses," J Virol., 2002, 76(10): 5266-5270.
Feng et al., "ABCA1-mediated Cholesterol Efflux is Defective in Free Cholesterol-loaded Macrophages," J Biol Chem., 2002, 277(45): 43271-43280.
Fischer et al., "N-Butyldeoxynojirimycin-Mediated Inhibition of Human Immunodeficiency Virus Entry Correlates with Changes in Antibody Recognition of the V1/V2 Region of gp120," Journal of Virology, Oct. 1996, 70(10):7143-7152.
Fischer et al., "N-Butyldeoxynojirimycin-Mediated Inhibition of Human Immunodeficiency Virus Entry Correlates with Impaired gp120 Shedding and gp41 Exposure," Journal of Virology, Oct. 1996, 70(10):7153-7160.
Fischer et al., "The α-Glucosidase Inhibitor N-Butyldeoxynojirimycin Inhibits Human Immunodeficiency Virus Entry at the Level of Post-CD4 Binding," Journal of Virology, Sep. 1995, 69(9):5791-5797.
Fischl et al., "The Safety and Efficacy of Combination N-Butyl-Deoxynojirimycin (SC-48334) and Zidovudine in Patients with HIV-1 Infection and 200-500 CD4 Cells/mm$^3$," Journal of Acquired Immune Deficiency Syndromes, 1994, 7:139-147.
Fleet et al., "Enantiospecific synthesis of deoxymannojirimycin, fagomine and 2R,5R-dihydroxymethyl-3R,4R-dihydroxypyrrolidine from D-glucose," Tetrahedron Letters, 1985, 26(11):1469-1472.
Giguere et al., "Statin Compounds Reduce Human Immunodeficiency Virus Type 1 Replication by Preventing the Interaction between Virion-Associated Host Intercellular Adhesion Molecule 1 and Its Natural Cell Surface Ligand LFA-1," J Virol., 2004, 78(21): 12062-12065.

Goldstein et al., "Regulation of the mevalonate pathway," Nature, 1990, 343(6257): 425-430.
Graf et al., "The Class B, Type I Scavenger Receptor Promotes the Selective Uptake of High Density Lipoprotein Cholesterol Ethers into Caveolae," J Biol Chem., 1999, 274(17): 12043-12048.
Graham et al., "Cholesterol Depletion of Human Immunodeficiency Virus Type 1 and Simian Immunodeficiency Virus with β-Cyclodextrin Inactivates and Permeabilizes the Virions: Evidence for Virion-Associated Lipid Rafts," J Virol., 2003, 77(15): 8237-8248.
Guyader et al., "Role for Human Immunodeficiency Virus Type 1 Membrane Cholesterol in Viral Internalization," J Virol., 2002, 76(20): 10356-10364.
Hajjar et al., "Lipoprotein Trafficking in Vascular Cells," J Biol Chem., 1997, 272(37): 22975-22978.
Holm et al., "Human Immunodeficiency Virus Type 1 Assembly and Lipid Rafts: Pr55$^{gag}$ Associates with Membrane Domains that are Largely Resistant to Brij$^{98}$ but Sensitive to Triton X-100," J Virol., 2003, 77(8): 4805-4817.
Hsue et al., "Progression of Atherosclerosis as Assessed by Carotid Intima-Media Thickness in Patients with HIV Infection," Circulation, 2004, 109(13): 1603-1608.
Hsue et al., "What a Cardiologist Needs to Know About Patients with Human Immunodeficiency Virus Infection," Circulation, 2005, 112(25): 3947-3957.
International Search Report in PCT/IB2009/005547 mailed Oct. 21, 2009, 6 pages.
Itzhaki et al., "Herpes simplex virus type 1, apolipoprotein E, and cholesterol: A dangerous liaison in Alzheimer's disease and other disorders," Prog Lipid Res., 2006, 45(1): 73-90.
Jain et al., "Anti-Inflammatory Effects of Statins: Clinical Evidence and Basic Mechanisms," Nat Rev Drug Discov, 2005, 4(12): 977-987.
Kapadia et al., "Initiation of Hepatitis C Virus Infection is Dependent on Cholesterol and Cooperativity between CD81 and Scavenger Receptor B Type I," J Virol., 2007, 81(1): 374-383.
Katzman et al., "Cholesterol-dependent infection of Burkitt's lymphoma cell lines by Epstein-Barr virus," J Gen Virol., 2003, 84(11): 2987-2992.
Kaur et al., "A correlation between membrane cholesterol level, cell adhesion and tumourigenicity of polyoma virus transformed cells," Mol Cell Biochem., 2004, 265(1-2): 85-95.
Lavillette et al., "Hepatitis C Virus Glycoproteins Mediate Low pH-dependent Membrane Fusion with Liposomes," J Biol Chem., 2006, 281(7): 3909-3917.
Leser et al., "Influenza virus assembly and budding in raft-derived microdomains: A quantitative analysis of the surface distribution of HA, NA and M2 proteins," Virology, 2005, 342(2): 215-227.
Locarnini et al., "Hepatitis B: New approaches for antiviral chemotherapy," Antiviral Chemistry & Chemotherapy, 1996, 7(2):53-64.
Lusis, A. J., "Atherosclerosis," Nature, 2000, 407(6801): 233-241.
Mañes et al., "Membrane raft microdomains mediate lateral assemblies required for HIV-1 infection," EMBO Rep., 2000, 1(2): 190-196.
Manie et al., "Measles Virus Structural Components Are Enriched into Lipid Raft Microdomains: a Potential Cellular Location for Virus Assembly," J Virol., 2000, 74(1): 305-311.
Nguyen et al., "Dynamic reorganization of chemokine receptors, cholesterol, lipid rafts, and adhesion molecules to sites of CD4 engagement," Exp Cell Res., 2005, 304(2): 559-569.
Nguyen et al., "Evidence for Budding of Human Immunodeficiency Virus Type 1 Selectively from Glycolipid-Enriched Membrane Lipid Rafts," J Virol., 2000, 74(7): 3264-3272.
Nishibori et al., "The Regulation of ICAM-1 and LFA-1 Interaction by Autacoids and Statins: a Novel Strategy for Controlling Inflammation and Immune Responses," J Pharmacol Sci., 2003, 92(1): 7-12.
Notification, International Search Report and Written Opinion of the International Searching Authority, mailed Dec. 22, 2008, in PCT/US2007/075080, 16 pages.
Ono et al., "Plasma membrane rafts play a critical role in HIV-1 assembly and release," Proc Natl Acad Sci U S A., 2001, 98(24): 13925-13930.

(56) References Cited

OTHER PUBLICATIONS

Oram, J. F., "Tangier disease and ABCA1," Biochim Biophys Acta., 2000, 1529(1-3): 321-330.
Percherancier et al., "HIV-1 Entry into T-cells Is Not Dependent on CD4 and CCR5 Localization to Sphingolipid-enriched, Detergent-resistant, Raft Membrane Domains," J Biol Chem., 2003, 278(5): 3153-3161.
Peterson et al., "Transient, Lectin-like Association of Calreticulin with Folding Intermediates of Cellular and Viral Glycoproteins," Molecular Biology of the Cell, Sep. 1995, 6:1173-1184.
Popik et al., "CD4 Receptor Localized to Non-raft Membrane Microdomains Supports HIV-1 Entry," J Biol Chem., 2004, 279(1): 704-712.
Reyes-del Valle et al., "Heat Shock Protein 90 and Heat Shock Protein 70 are Components of Dengue Virus Receptor Complex in Human Cells," J Virol., 2005, 79(8): 4557-4567.
Rhainds et al., "Localization and regulation of SR-BI in membrane rafts of HepG2 cells," J Cell Sci, 2004, 117(15): 3095-3105.
Salzwedel et al., "Sequential CD4-Coreceptor Interactions in Human Immunodeficiency Virus Type 1 Env Function: Soluble CD4 Activates Env for Coreceptor-Dependent Fusion and Reveals Blocking Activities of Antibodies against Cryptic Conserved Epitopes on gp120," Journal of Virology, Jan. 2000, 74(1):326-333.
Scheiffele et al., "Influenza Viruses Select Ordered Lipid Domains during Budding from the Plasma Membrane," J Biol Chem., 1999, 274(4): 2038-2044.
Simoes et al., "On the mechanisms of internalization and intracellular delivery mediated by pH-sensitive liposomes," Biochimica et Biophysica Acta, 2001, 1515:23-37.
Slepushkin et al., "Sterically Stabilized pH-sensitive Liposomes," J. Biol. Chem., Jan. 24, 1998, 272(4):2382-2388.
Soldaini et al., "T cell costimulation by the hepatitis C virus envelope protein E2 binding to CD81 is mediated by Lck," Eur J Immunol., 2003, 33(2): 455-464.
Steinberg et al., "Beyond Cholesterol: Modification of Low-Density Lipoprotein That Increase Its Atherogenicity," N Engl J Med., 1989, 320(14): 915-924.
Sun et al., "Role for Influenza Virus Envelope Cholesterol in Virus Entry and Infection," J Virol., 2003, 77(23): 12543-12551.
Tabas, Ira, "Cholesterol in health and disease," J Clin Invest., 2002, 110: 583-590.
Tabas, Ira, "Consequences of cellular cholesterol accumulation: basic concepts and physiological implications," J Clin Invest., 2002, 110: 905-911.
Takeda et al., "Influenza virus hemagglutinin concentrates in lipid raft microdomains for efficient viral fusion," Proc Natl Acad Sci U S A., 2003, 100: 14610-14617.
Ulrich et al., "Biophysical Aspects of Using Liposomes as Delivery Vehicles," Bioscience Reports, Apr. 2002, 22(2):129-150.
van Wijk et al., "Functional and Structural Markers of Atherosclerosis in Human Immunodeficiency Virus-Infected Patients," J Am Coll Cardiol., 2006, 47(6): 1117-1123.
Viard et al., "Role of Cholesterol in Human Immunodeficiency Virus Type 1 Envelope Protein-Mediated Fusion with Host Cells," J Virol., 2002, 76(22): 11584-11595.
Vincent et al., "Measles Virus Assembly within Membrane Rafts," J Virol., 2000, 74(21): 9911-9915.
Who, "Global surveillance and control of hepatitis C," J. Viral Hepatitis, 1999, 6:35-47.
Zitzmann et al., "Imino sugars inhibit the formation and secretion of bovine viral diarrhea virus, a pestivirus model of hepatitis C virus: Implications for the development of broad spectrum anti-hepatitis virus agents," PNAS, Oct. 12, 1999, 96(21):11878-11882.
Holland et al., "Poly(ethylene glycol)-Lipid Conjugates Regulate the Calcium-Induces Fusion of Liposomes Composed of Phosphatidylethanolamine and Phosphatidylserine," Biochemistry, 1996, 35:2618-2624.
Miyanari et al., "The lipid droplet is an important organelle for hepatitis C virus production," Nature Cell Biology, Sep. 2007, 9(9):1089-1097 (actually 961-969) with 14 pages of Supplementary Information.
Ma et al., "Effects of docosahesaenoic acid-phosphatidylcholine on the lipid metabolism in normal mice," Chin. J. Mar. Drugs, Dec. 2008, 27(6):31-34, English abstract on first page.

\* cited by examiner

FIGURES 2 A-F
A. 22:6 PE
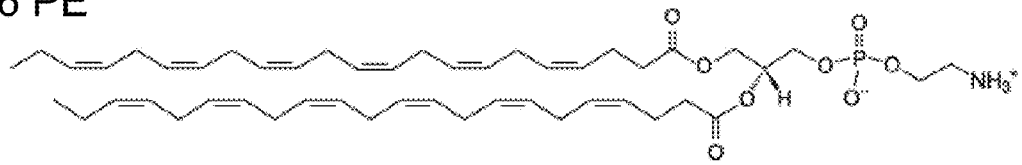
B. 22:6 PC
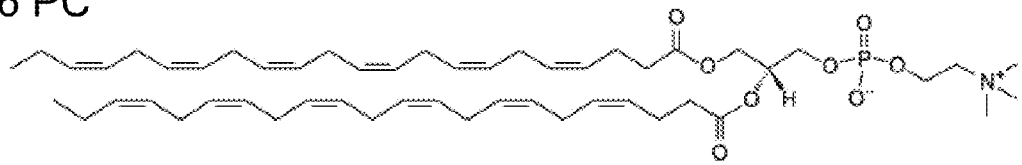
C. PI
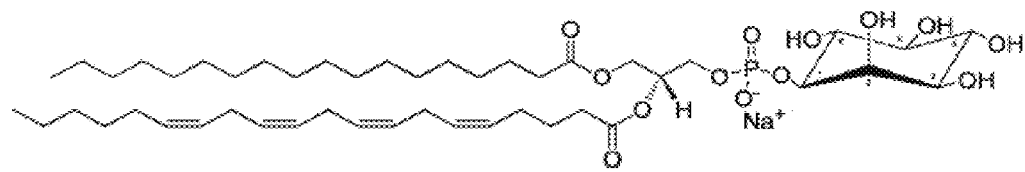
D. PS
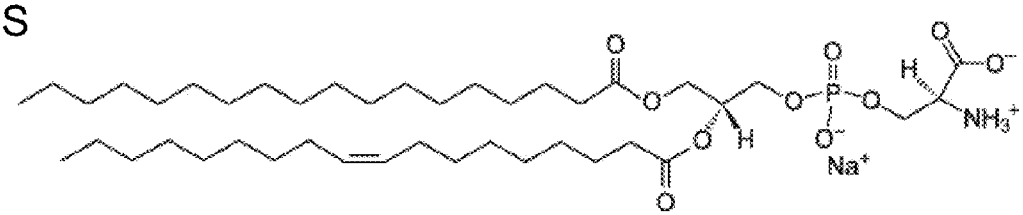
E. DOPE
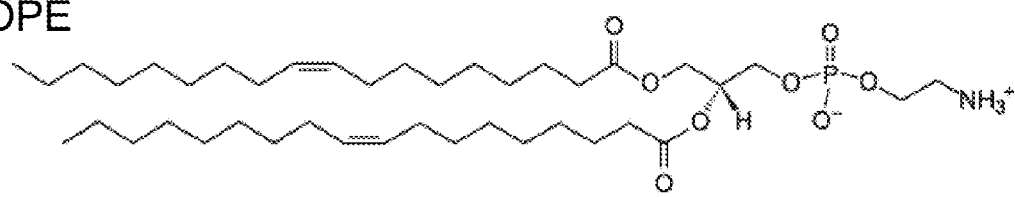
F. CHEMS
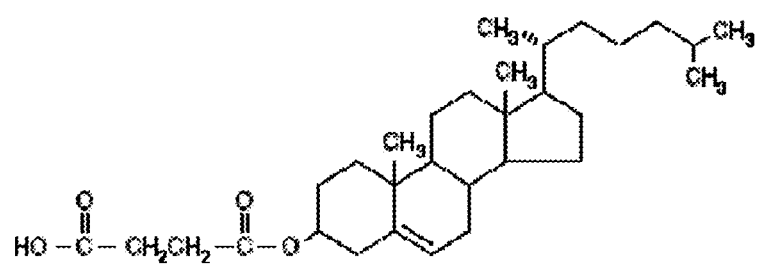

FIGURES 6A-E

FIGURES 9A-B
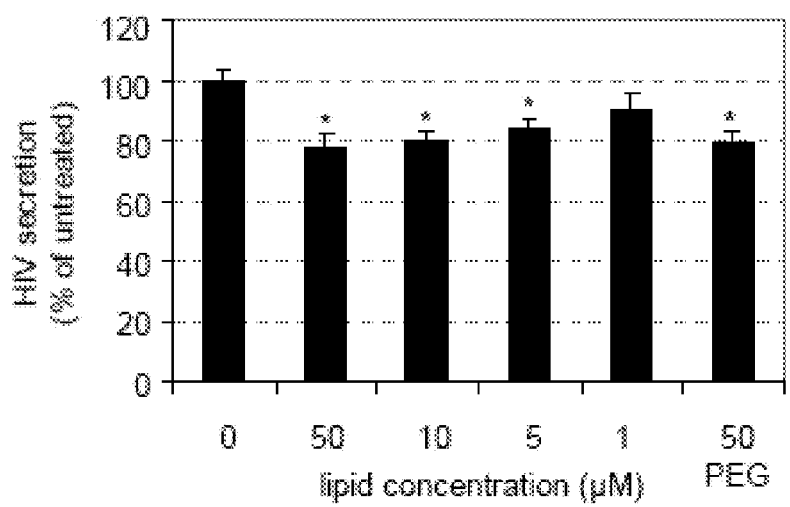
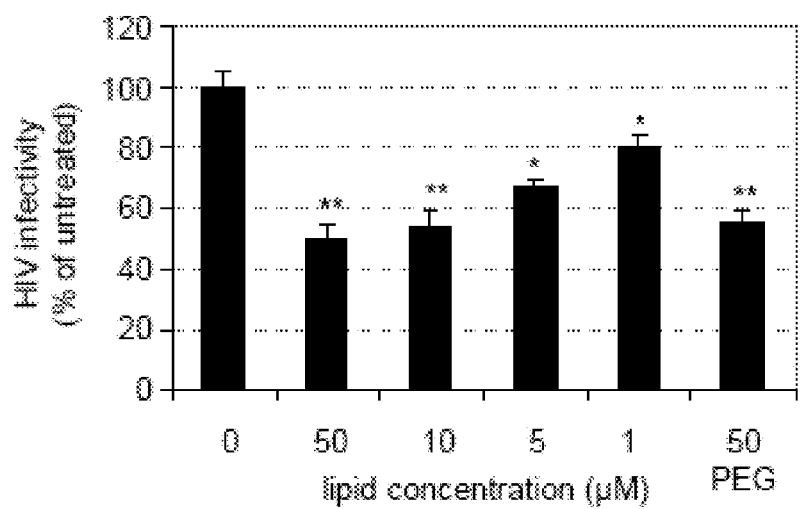

CHOLESTEROL LEVEL LOWERING LIPOSOMES

RELATED APPLICATIONS

The present application claims priority to U.S. provisional application No. 61/202,699 filed Mar. 27, 2009, which is incorporated herein in its entirety.

FIELD

The present application relates generally to lipid particles, such as liposomes which are themselves useful as a therapeutic or which may be used for drug delivery, methods of drug delivery and, in particular, to methods of drug delivery utilizing lipid particles, such as liposomes.

SUMMARY

A method of reducing an cellular cholesterol level comprises administering to a subject in need thereof a composition comprising a lipid particle, such as a liposome or micelle, that are capable of cellular entry.

FIGURES

FIG. 1 shows a) mevalonate pathway and isoprenoid synthesis and b) the effects of different therapeutic agents on different cellular targets. PP=pyrophosphate, FTIs=farnesyl transferase inhibitors, GGTIs=geranylgeranyl transferase inhibitors, IPP=isopentyl pyrophosphate.

FIG. 2 schematically illustrates the selected lipids: A) 22:6 PE; B) 22:6 PC; C) PI; D) PS; E) DOPE; F) CHEMS.

FIG. 3 presents results of Western blot analysis of 22:6 ER liposome-treated, JC-1-infected Huh7.5 cells (MOI=0.5) using both anti-actin and anti-HMGCS antibodies.

FIG. 4 presents quantification results for both free and total cholesterol from 22:6 PE:22:6 PC:PI:PS-treated, JC1-infected Huh7.5 cells (MOI=0.5).

FIG. 5 presents quantification results for PHA-stimulated PBMCs treated with 22:6 liposomes.

FIGS. 6(A)-(E) present data related to treatment of JC-1-infected Huh7.5 cells (MOI=0.02) with 22:6 ER liposomes for 16 days. (A) JC-1 HCVcc infection levels in Huh7.5 cells throughout treatment. (B) JC-1 HCVcc secretion. (C) Infectivity of secreted JC-1 HCVcc particles. (D) Free cholesterol levels in cells. (E) Esterified cholesterol in cells. Data represent the average of triplicate samples from two independent experiments.

FIG. 7 presents infectivity data for 22:6 ER liposome-treated, PEGyated 22:6 ER liposome-treated and untreated JC-1 HCVcc treated with exogenous cholesterol (final concentrations of 15 μg/ml and 150 μg/ml cholesterol).

FIG. 8 presents quantification results for uninfected Huh7.5 cells treated with 22:6 ER liposomes for 4 days prior to infection with JC-1 HCVcc (MOI=0.5).

FIG. 9 (A) shows average secretion of three genetically diverse primary isolates of HIV-1 (LAI, 93UG067, and 93RW024) during a 4 day treatment with 22:6 ER liposomes. FIG. 9 (B) shows infectivity of HIV-1 secreted from 22:6 ER liposome-treated PBMCs.

DETAILED DESCRIPTION

Definition of Terms

Figure 1:
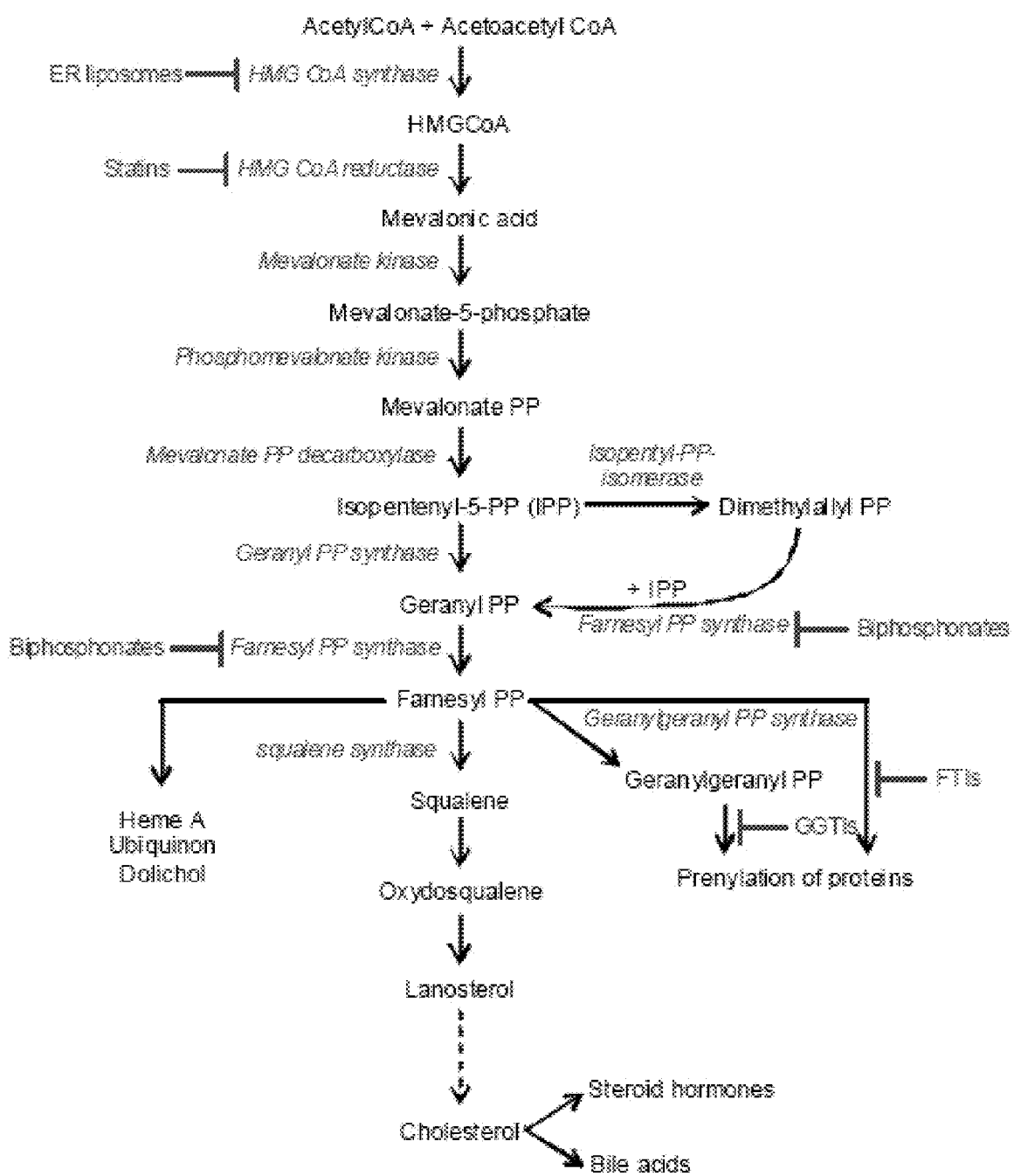

Unless otherwise specified, "a" or "an" means "one or more."

As used herein, the term "viral infection" describes a diseased state, in which a virus invades a healthy cell, uses the cell's reproductive machinery to multiply or replicate and ultimately lyse the cell resulting in cell death, release of viral particles and the infection of other cells by the newly produced progeny viruses. Latent infection by certain viruses is also a possible result of viral infection.

As used herein, the term "treating or preventing viral infection" means to inhibit the replication of the particular virus, to inhibit viral transmission, or to prevent the virus from establishing itself in its host, and to ameliorate or alleviate the symptoms of the disease caused by the viral infection. The treatment is considered therapeutic if there is a reduction in viral load, decrease in mortality and/or morbidity.

The term "therapeutic agent" refers to an agent, such as a molecule or a compound, which can assist in treating a physiological condition, such as a viral infection or a disease caused thereby.

The term "liposome" may be defined as a particle comprising lipids in a bilayer formation, which is usually a spherical bilayer formation. The term "liposome" encompasses both unilamellal liposomes and multilamellar liposomes. Liposomes discussed herein may include one or more lipids represented by the following abbreviations:
CHEMS stands for cholesteryl hemisuccinate lipid.
DOPE stands for dioleoylphosphatidylethanolamine lipid.
DOPC stands for dioleoylphosphatidylcholine lipid.
PE stands for phosphatidylethanolamine lipid or its derivative.
PEG-PE stands for PE lipid conjugated with polyethylene glycol (PEG). One example of
PEG-PE can be polyethylene glycol-distearoylphosphatidylethanolamine lipid. Molecular weight of PEG component of PEG may vary.
Rh-PE stands for lissamine rhodamine B-phosphatidylethanolamine lipid.
MCC-PE stands for 1,2-Dioleoyl-sn-Glycero-3-Phosphoethanolamine-N-[4-(p-maleimidomethyl)cyclohexane-carboxamide] lipid.
PI stands for phosphatidylinositol lipid.
PS stands for phosphatidylserine lipid.

The term "intracellular delivery" can refer to the delivery of encapsulated material from liposomes into any intracellular compartment.

IC50 or IC90 (inhibitory concentration 50 or 90) can refer to a concentration of a therapeutic agent used to achieve 50% or 90% reduction of viral infection, respectively.

PBMC stands for peripheral blood mononuclear cell.

sCD4 stands for a soluble CD4 molecule. By "soluble CD4" or "sCD4" or "D1D2" is meant a CD4 molecule, or a fragment thereof, that is in aqueous solution and that can mimic the activity of native membrane-anchored CD4 by altering the conformation of HIV Env, as is understood by those of ordinary skill in the art. One example of a soluble CD4 is the two-domain soluble CD4 (sCD4 or D1D2) described, e.g., in Salzwedel et al. J. Virol. 74:326 333, 2000.

MAb stands for a monoclonal antibody.

DNJ denotes deoxynojirimycin.

NB-DNJ denotes N-butyl deoxynojirimycin.

NN-DNJ denotes N-nonyl deoxynojirimycin.
BVDV stands for bovine viral diarrhea virus.
HBV stands for hepatitis B virus.
HCV stands for hepatitis C virus.
HIV stands for human immunodeficiency virus.
Ncp stands for non-cytopathic.
Cp stands for cytopathic.
ER stands for endoplasmic reticulum.
CHO stands for Chinese hamster ovary cells
MDBK stands for Madin-Darby bovine kidney cells.
PCR stands for polymerase chain reaction.
FOS stands for free oligosaccharides.
HPLC stands for high performance liquid chromatography.
PHA stands for phytohemagglutinin.
FBS stands for fetal bovine serum.
TCID50 stands for 50% tissue culture infective dose.
ELISA stands for Enzyme Linked Immunosorbent Assay.
IgG stands for immunoglobuline.
DAPI stands for 4',6-Diamidino-2-phenylindole.
PBS stands for phosphate buffered saline.
LD stands for lipid droplet.
NS stands for non-structural.
"MOI" refers to multiplicity of infection.
DMEM refers to Dulbecco's Modified Eagle Medium.

RELATED DOCUMENTS

The present disclosure incorporates by reference in their entirety US patent publications nos. 20080138351; 20090252785; and 20030124160.

Macrophages and Cholesterol Metabolism

Macrophages, like other cells except hepatocytes, are not capable of degrading cholesterol to any appreciable extent. Cell cholesterol content therefore may be essentially a balance between cholesterol intake and cholesterol efflux. Two major mechanisms of cholesterol delivery to cells may be receptor-mediated uptake of plasma low-density lipoprotein (LDL) and intracellular cholesterol biosynthesis. Each of these two major pathways of cholesterol delivery may fully satisfy the needs of a cell in case of cholesterol deficiency, and both may be highly regulated (Brown and Goldstein 1999, for complete citation, see section REFERENCES below). However, in some pathophysiological conditions, such as inflammation, high plasma LDL concentration and oxidative stress may lead to the formation of modified, mostly oxidized, LDL (Steinberg, Parthasarathy et al. 1989). Modified LDL may interact with scavenger receptors (SRs) expressed on several cell types, including macrophages. The uptake of modified lipoproteins is not regulated in response to cell cholesterol content and may result in uncontrollable delivery of excessive cholesterol to macrophages (Hajjar and Haberland 1997; Dhaliwal and Steinbrecher 2000). If not compensated by increased cholesterol efflux, this may lead to the accumulation of cholesterol and formation of lipid-laden foam cells, followed by development of a fatty streak in the arterial wall, one of the earliest steps in the progression of atherosclerotic plaques. Cholesterol-laden macrophages may be also a likely trigger for other elements of the pathogenesis of atherosclerosis, such as perpetuation of inflammation, phenotypical modification of smooth muscle cells, and overproduction of extracellular matrix proteins (Lusis 2000). Excess of cholesterol may be compensated by down-regulating cholesterol biosynthesis and expression of LDL receptors. However, the ability of cells to compensate for severe excess of cholesterol delivered by modified LDL by diminishing LDL uptake and cholesterol synthesis may be limited. Two other mechanisms to compensate for excess of free cholesterol may be synthesis of cholesteryl esters and cholesterol efflux. Although cholesteryl ester synthesis may provide temporary relief, continuous production of cholesteryl esters may lead to excessive accumulation of intracellular lipid droplets. Overloading of macrophages with cholesterol may lead to their apoptosis and necrosis, contributing to the necrotic and calcified core of the late atherosclerotic plaque (Tabas 2002; Tabas 2002).

The Mevalonate Pathway for Cholesterol Biosynthesis in Cells

The first step in the mevalonate-isoprenoid pathway may involve the synthesis of 3-hydroxy-3-methylglutaryl (HMG)-CoA from acetyl-CoA through acetoacetylCoA by the action of HMG-CoA synthase (HMGCS). HMG-CoA reductase (HMGCR), one of the most highly regulated enzymes in nature, can catalyze the conversion of HMG-CoA to mevalonic acid (Goldstein and Brown 1990). Rational therapeutic manipulation of the mevalonate pathway and downstream isoprenoid biosynthesis pathway by statins and biphosphonates has been intensively studied and found to be an interesting and revolutionary option in a variety of diseases (Buhaescu and Izzedine 2007). FIG. 1 presents the mevalonate pathway and isoprenoid biosynthesis. The effect of certain key therapeutics on their different cellular targets is also represented.

Cholesterol and Viral Replication

A number of viruses may depend on cholesterol for their replication. Such viruses include, but not limited to, viruses belonging to the Herpesviridae family, such as herpes simplex virus (see e.g. Itzhaki and Wozniak 2006), which may HSV 1 or HSV 2 virus, and Epstein-Barr virus (see e.g. Katzman and Longnecker 2003); viruses belonging to the Orthomyxoviridae family, such as an influenza virus (see e.g. Sun and Whittaker 2003), which may be an Influenza virus A, Influenza virus B or Influenza virus C; a retrovirus, such as murine leukemia virus (see e.g. Beer, Pedersen et al. 2005) and human immunodeficiency virus (HIV) (see e.g. Mañes, del Real et al. 2000; Campbell, Crowe et al. 2001), which HIV 1 or HIV 2 virus; viruses belonging to the Poxyiridae family, such as vaccinia virus (see e.g. Chung, Huang et al. 2005); polyoma virus (see e.g. Kaur, Gopalakrishna et al. 2004); viruses belonging to the Togaviridae family, such as Semiliki Forest virus (see e.g. Chatterjee, Eng et al. 2002); viruses belonging to the Filoviridae family, such as Ebola virus (see e.g. Empig and Goldsmith 2002) and Marburg virus (see e.g. Bavari, Bosio et al. 2002); viruses belonging to the Flaviviridae family, including viruses belonging the *Flavivirus* genus, such as dengue virus (see e.g. Reyes-del Valle, Chavez-Salinas et al. 2005) and viruses belonging to the Hepacivirus genus, such as hepatitis C virus (HCV) (see e.g. Aizaki, Morikawa et al. 2008); viruses belonging to the Paramyxoviridae family, such as measles virus (see e.g. Manie, Debreyne et al. 2000), and viruses belonging to the Hepadnaviridae family, such as hepatitis B virus (HBV) (see e.g. Bremer, Bung et al. 2009). Not all of these viruses may infect macrophages, indicating that cholesterol requirement is not limited to infection of a particular cell type. Despite the wide acknowledgement that cholesterol may be an important component of the membrane of enveloped viruses, surprisingly little is known about why and how cholesterol is involved in viral replication. Most of the knowledge about the role of cholesterol in viral replication can be limited to the function of lipid rafts, the sphingolipid- and cholesterol-enriched microdomains of the plasma membrane. Several enveloped viruses can use raft-like domains as platforms for virus assembly, e.g., HIV (Campbell, Crowe et al. 2001), Ebola and Marburg viruses (Bavari, Bosio et al. 2002), measles virus (Vincent, Gerlier et al. 2000), and influenza virus (Scheiffele, Rietveld et al. 1999; Leser and Lamb 2005). Lipid rafts may also be used as entry points during viral infection, as suggested for influenza virus, based on the finding that hemagglutinin concentrates in lipid rafts (Takeda, Leser et al. 2003).

Effects of Cholesterol Depletion on HIV

The effect of cholesterol depletion on HIV replication may also be indirect, resulting from multiple changes in cellular metabolism in response to changes in cellular cholesterol content and/or rate of cholesterol biosynthesis. For example, inhibition of cholesterol biosynthesis by statins may reduce the steady concentration of all intermediates upstream of HMG-CoA reductase, including those involved in protein prenylation (Buhaescu and Izzedine 2007). Reduction of prenylation of small G-proteins may lead to inhibition of the Rho-guanosinetriphosphatase (GTPase) and Rho-A activation, resulting in reduced virus entry (del Real, Jimenez-Baranda et al. 2004). In addition, statins may have pleiotropic beneficial effects independent of their effect on cholesterol biosynthesis, which may reduce HIV infection. These effects may include anti-inflammatory properties resulting from the ability of statins to inhibit expression of the adhesion molecules (Jain and Ridker 2005) or interaction of receptor-ligand pairs, such as ICAM-1 and LFA-1, on the endothelium and leukocytes (Nishibori, K. Takahashi et al. 2003). Inhibition of interaction of ICAM-1 with LFA-1 by statins may diminish HIV attachment to cells (Giguere and Tremblay 2004). Many studies have investigated the role of cholesterol in the life cycle of HIV. HIV-1 budding from the host cell occurs at the lipid rafts, resulting in the high cholesterol: phospholipid molar ratio (>1.0) of the viral envelope (Aloia, Tian et al. 1993; Nguyen and Hildreth 2000). This affinity for rafts may be determined by the Gag precursor, which specifically may associate with these membrane domains (Ono and Freed 2001; Ding, Derdowski et al. 2003; Holm, Weclewicz et al. 2003). Lipid-raft binding may be mediated by the N-terminus of Gag and can be greatly enhanced by the Gag-Gag interaction domains. Depletion of cellular cholesterol and decrease in the number of rafts markedly and specifically may reduce HIV-1 particle production (Ono and Freed 2001). In addition to the indirect effects of cholesterol-lowering drugs on HIV entry described above, several studies have proposed a role for lipid rafts as entry points for HIV. This model relies on the phenomenon of cocapping of CD4, the HIV cellular receptor, and chemokine receptors at the sites of HIV entry (Alfano, Schmidtmayerova et al. 1999), which may be also dependent on cholesterol (Nguyen, Giri et al. 2005). A study by Viard and others (Viard, Parolini et al. 2002) demonstrated that cholesterol-depleted cells may be unable to form clusters of CD4 and CXCR4 (or CCR5) necessary for virus-cell fusion. A similar observation was reported by Manes et at (Mañes, del Real et al. 2000), who proposed a role for gp120-induced lateral reorganization of rafts to bring the CD4-120 complexes together with a raft-associated chemokine receptor. However, later reports demonstrated that association of CD4 and chemokine receptors with rafts may not be necessary for HIV infection (Percherancier, Lagane et al. 2003; Popik and Alce 2004). The usual caveat of these findings may be that many of them were done using cells overexpressing HIV receptors. Such cells often may behave differently from primary cells, as demonstrated previously for signaling from chemokine receptors, which may be essential for HIV entry into primary cells (Alfano, Schmidtmayerova et al. 1999). What all these papers agree on is the dependence of HIV entry on cholesterol in the target cell membrane, as depletion of cholesterol inhibited HIV entry mediated by raft-associated and raft-excluded CD4 (Popik and Alce 2004).

The importance of cholesterol for infectivity of HIV virions was demonstrated by experiments where treatment of HIV particles with cholesterol-sequestering drugs, such as MβCD, rendered the virus incompetent for cell entry (Campbell, Crowe et al. 2002; Guyader, Kiyokawa et al. 2002). Cholesterol-depleted HIV-1 virions may exhibit disruptions of the virion lipid bilayer (Campbell, Crowe et al. 2002) yet may display normal levels of gp120 Env (Guyader, Kiyokawa et al. 2002). One study demonstrated MβCD may permeabilize the viral membrane, resulting in the loss of mature Gag proteins (capsid matrix, and p6) without the loss of the Env glycoproteins (Graham, Chertova et al. 2003). Electron microscopy revealed holes in the viral membrane of cholesterol-depleted virions and perturbations of the viral core structure (Graham, Chertova et al. 2003).

HIV and Atherosclerosis

HIV infection may be consistently associated with increased risk of development of atherosclerosis (Hsue, Lo et al. 2004; van Wijk, de Koning et al. 2006) and at least a threefold increased risk of coronary artery disease (CAD) (Hsue and Waters 2005). This association was previously attributed exclusively to the adverse effects of antiretroviral therapy. Although many changes in cholesterol metabolism, such as elevation of LDL (El-Sadr, Mullin et al. 2005) and increased cholesterol uptake through induction of CD36 expression (Allred, Smart et al. 2006), may be likely to be caused by antiretroviral therapy (Carpentier, Patterson et al. 2005), the relative contributions of therapy and the HIV infection itself to changes in cholesterol metabolism may remain to be determined. Preliminary studies may indicate that HIV infection itself might play a key role in increasing the risk of CAD. HIV may infect macrophages and impair reverse cholesterol transport in these cells. Impairment of cholesterol efflux from macrophages may lead to accumulation of intracellular cholesterol (Feng and Tabas 2002) and development of atherosclerosis in animal models (Aiello, Brees et al. 2002) and in humans (Oram 2000). This process may be especially rapid when associated with dyslipidemia. It may be suggested that infection of macrophages with HIV, when associated with dyslipidemia caused by antiretroviral therapy, may cause accumulation of cholesterol in macrophages and rapid development of atherosclerosis.

Cellular Cholesterol and HCV

HCV infection is mainly restricted to hepatocytes (Chisari 2005), which may play a vital role in mammalian cholesterol homeostasis. Localization to cholesterol-enriched plasma membrane microdomains (or lipid rafts) has been demonstrated for both CD81 (Soldaini, Wack et al. 2003; Cherukuri, Shoham et al. 2004) and SR-BI (Rhainds, Bourgeois et al. 2004), two cellular receptors necessary for HCV entry into cells. SR-BI may be associated with cholesterol-enriched plasma membrane microdomains called caveolae (Babitt, Trigatti et al. 1997; Graf, Connell et al. 1999). CD81 has been demonstrated to interact physically with cholesterol (Charrin, Manié et al. 2003). While the dependence of HCV infection on cellular cholesterol may be currently unknown, HCVpp fusion with liposomes may be enhanced by the presence of cholesterol in the target membrane (Lavillette, Bartosch et al. 2006). These data may strongly suggest that plasma membrane cholesterol may be required for HCV entry. It has been demonstrated that HCV infection may be dependent on a cooperative interaction between CD81 and SR-BI and that cellular cholesterol content may have a significant impact on HCV entry, possibly by regulating cell surface expression and localization of CD81 (Kapadia, Barth et al. 2007).

Recent studies have shown important roles for cholesterol and sphingolipid in HCV infection and virion maturation. Specifically, mature HCV particles can be rich in cholesterol (Aizaki, Morikawa et al. 2008). Depletion from HCV or hydrolysis of virion-associated SM results in a loss of infectivity (Aizaki, Morikawa et al. 2008). Moreover, the addition of exogenous cholesterol can restore infectivity. In addition, portions of structural proteins can be localized at lipid-raft-like membrane structures within cells (Aizaki, Lee et al. 2004).

DISCLOSURE

The present inventors discovered that lipid particles, such as liposomes, which may be capable of cellular entry and/or intracellular delivery of material encapsulated inside of the particle, may inhibit cholesterol biosynthesis by downregulating one of the first enzymes involved in this pathway, HMGCS.

In some embodiments, the lipid particles may contain at least one PE lipid and/or a derivative thereof. Examples of derivatives PE lipids include DOPE and conjugated PE lipids. The conjugated PE lipids may include PE lipids conjugated with a hydrophilic polymer such as polyethylene glycol and PE lipids conjugated with a label such as a fluorescent label. The PE lipid may be monosaturated or polysaturated.

In some embodiments, the lipid particles may include one or more PI, PS, PC and CHEMS lipids, each of which may be monosaturated or polysaturated.

In some embodiments, the lipid particles may contain one or more lipids conjugated with a hydrophilic polymer such as polyethylene glycol. Molecular weight of the hydrophilic polymer may vary. The use of conjugated hydrophilic polymers may increase the in vivo stability and circulation time of the lipid particle.

In some embodiments, the lipid particles that are capable of cholesterol inhibition may be lipid particles containing PE lipids and/or derivatives thereof and CHEMS lipids, such as pH-sensitive liposomes disclosed in U.S. patent publication No. 20080138351. For example, such lipid particles can be DOPE-CHEMS liposomes with a molar ratio 6:4 or 6:3 or DOPE:CHEMS:PEG-PE with a molar ratio 6:3:0.1.

In some embodiments, the lipid particles that are capable of cholesterol inhibition may be lipid particles containing PE lipids and/or derivatives thereof, and PI and/or PS lipids. Examples of such lipid particles include ER-targeting liposomes disclosed in U.S. patent application Ser. No. 12/410,750 filed Mar. 25, 2009. In some embodiments, the lipid particles may be lipid particles that include PE, PI, PS and PC lipids, each of which may be monosaturated or polysaturated.

In some embodiments, the lipid particles that are capable of cholesterol inhibition may be polyunsaturated lipid particles, i.e. lipid particles that that include at least one polyunsaturated lipid. As used herein, the term "polyunsaturated lipid" refers to a lipid that contains more than one unsaturated chemical bond, such as a double or a triple bond, in its hydrophobic tail. In some embodiments, the polyunsaturated lipid can have from 2 to 8 or from 3 to 7 or from 4 to 6 double bonds in its hydrophobic tail. Polyunsaturated lipid particles are disclosed in US patent publication no. 20090252785. Examples of polyunsaturated lipids are presented in FIGS. 2A-B as well as in FIGS. 22A-D of US patent publication no. 20090252785.

Targeting Moieties

In some embodiments, the composition comprising the lipid particle may comprise at least one targeting moiety, which can be conjugated with the lipid particle or intercalated into a lipid layer or bilayer of the particle. In some embodiments, the targeting moiety may be a ligand, which may be a ligand of an envelope protein of a virus, or an antibody, which may be an antibody against an envelope protein of a virus. Such a moiety may used for targeting the particle to a cell infected with the virus. Such targeting moiety may be also used for achieving sterilizing immunity against a viral infection associated with or caused by the virus. In some embodiments, the targeting moiety may comprise with a gp120/gp41 targeting moiety. In such a case, the composition comprising the lipid particle may be preferred for treating and/or preventing an HIV-1 infection. The gp120/gp41 targeting moiety can comprise a sCD4 molecule or a monoclonal antibody, such as IgG 2F5 or IgG b12 antibodies. In some embodiments, the targeting moiety can comprise E1 or E2 targeting moiety, such as E1 or E2 proteins from HCV. In such a case, the composition comprising the lipid particle may be preferred for treating and/or preventing an HCV infection. In some cases, targeting moiety may be also a molecule that can target E1 and/or E2 proteins, such as specific antibodies to these proteins, and soluble portions of cell receptors, such as a soluble CD81 or SR-BI molecules.

Active Agent

In some embodiments, at least one agent, such as a therapeutic agent or an imaging agent, may be encapsulated inside the lipid particle. Such an agent may be, for example, a water soluble molecule, a peptide or an amino acid.

In some embodiments, the agent encapsulated inside the lipid particle can be, an α-glucosidase inhibitor. In some embodiments, the α-glucosidase inhibitor can be ER α-glucosidase inhibitor, which may be ER α-glucosidase I inhibitor or ER α-glucosidase II inhibitor. In general, any virus that relies on interactions with calnexin and/or calreticulin for proper folding of its viral envelope glycoproteins, can be targeted with ER α-glucosidase inhibitor.

The alpha-glucosidase inhibitor may be an agent that inhibits host alpha-glucosidase enzymatic activity by at least about 10%, at least about 15%, at least about 20%, at least about 25%, at least about 30%, at least about 35%, at least about 40%, at least about 50%, at least about 60%, at least about 70%, at least about 80%, or at least about 90%, or more, compared to the enzymatic activity of the alpha-glucosidase in the absence of the agent. The term "alpha-glucosidase inhibitor" encompasses both naturally occurring and synthetic agents that inhibit host alpha-glucosidase activity.

Suitable alpha-glucosidase inhibitors may include, but not be limited to, deoxynojirimycin and N-substituted deoxynojirimycins, such as compounds of Formula I and pharmaceutically acceptable salts thereof:

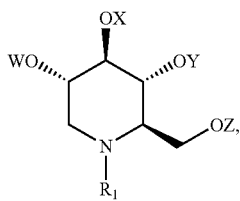

where $R_1$ is selected from substituted or unsubstituted alkyl groups, which can be branched or straight chain alkyl group; substituted or unsubstituted cycloalkyl groups; substituted or unsubstituted aryl groups, substituted or unsubstituted oxaalkyl groups, substituted or unsubstituted arylalkyl, cycloalkylalkyl, and where W, X, Y, and Z are each independently selected from hydrogen, alkanoyl groups, aroyl groups, and haloalkanoyl groups.

In some embodiments, $R_1$ can be selected from C1-C20 alkyl groups or C3-C12 alkyl groups.

In some embodiments, $R_1$ can be selected from ethyl, propyl, isopropyl, butyl, isobutyl, tert-butyl, pentyl, neopentyl, isopentyl, n-hexyl, heptyl, n-octyl, n-nonyl and n-decyl. In some embodiments, $R_1$ can be butyl or nonyl.

In some embodiments, $R_1$ can be an oxalkyl, which can be C1-C20 alkyl groups or C3-C12 alkyl group, which can also contain 1 to 5 or 1 to 3 or 1 to 2 oxygen atoms. Examples of oxalkyl groups include —$(CH_2)_2$—O—$(CH_2)_5CH_3$, —$(CH_2)_2$—O—$(CH_2)_6CH_3$, —$(CH_2)_6OCH_2CH_3$, and —$(CH_2)_2OCH_2CH_2CH_3$.

In some embodiments, $R_1$ can be an arylalkyl group. Examples of arylalkyl groups include C1-C12-Ph groups, such as C3-Ph, C4-Ph, C5-Ph, C6-Ph and C7-Ph.

In some embodiments, the compound of Formula I can be selected from, but is not limited to N-(n-hexyl-)-1,5-dideoxy-1,5-imino-D-glucitol; N-(n-heptyl-)-1,5-dideoxy-1,5-imino-D-glucitol; N-(n-octyl-)-1,5-dideoxy-1,5-imino-D-glucitol; N-(n-octyl-)-1,5-dideoxy-1,5-imino-D-glucitol, tetrabutyrate; N-(n-nonyl-)-1,5-dideoxy-1,5-imino-D-glucitol, tetrabutyrate; N-(n-decyl-)-1,5-dideoxy-1,5-imino-D-glucitol, tetrabutyrate; N-(n-undecyl-)-1,5-dideoxy-1,5-imino-D-glucitol, tetrabutyrate; N-(n-nonyl-)-1,5-dideoxy-1,5-imino-D-glucitol; N-(n-decyl-)-1,5-dideoxy-1,5-imino-D-glucitol; N-(n-undecyl-)-1,5-dideoxy-1,5-imino-D-glucitol; N-(n-dodecyl-)-1,5-dideoxy-1,5-imino-D-glucitol; N-(2-ethylhexyl)-1,5-dideoxy-1,5-imino-D-glucitol; N-(4-ethylhexyl)-1,5-dideoxy-1,5-imino-D-glucitol; N-(5-methylhexyl)-1,5-dideoxy-1,5-imino-D-glucitol; N-(3-propylhexyl)-1,5-dideoxy-1,5-imino-D-glucitol; N-(1-pentylpentylhexyl)-1,5-dideoxy-1,5-imino-D-glucitol; N-(1-butylbutyl)-1,5-dideoxy-1,5-imino-D-glucitol; N-(7-methyloctyl-)-1,5-dideoxy-1,5-imino-D-glucitol; N-(8-methylnonyl)-1,5-dideoxy-1,5-imino-D-glucitol; N-(9-methyldecyl)-1,5-dideoxy-1,5-imino-D-glucitol; N-(10-methylundecyl)-1,5-dideoxy-1,5-imino-D-glucitol; N-(6-cyclohexylhexyl-)-1,5-dideoxy-1,5-imino-D-glucitol; N-(4-cyclohexylbutyl)-1,5-dideoxy-1,5-imino-D-glucitol; N-(2-cyclohexylethyl)-1,5-dideoxy-1,5-imino-D-glucitol; N-(1-cyclohexylmethyl)-1,5-dideoxy-1,5-imino-D-glucitol; N-(1-phenylmethyl)-1,5-dideoxy-1,5-imino-D-glucitol, tetrabutyrate; N-(3-phenylpropyl)-1,5-dideoxy-1,5-imino-D-glucitol, tetrabutyrate; N-(n-dodecyl-)-1,5-dideoxy-1,5-imino-D-glucitol, tetrabutyrate; N-(2-ethylhexyl)-1,5-dideoxy-1,5-imino-D-glucitol, tetrabutyrate; N-(4-ethylhexyl)-1,5-dideoxy-1,5-imino-D-glucitol, tetrabutyrate; N-(5-methylhexyl)-1,5-dideoxy-1,5-imino-D-glucitol, tetrabutyrate; N-(3-propylhexyl)-1,5-dideoxy-1,5-imino-D-glucitol, tetrabutyrate; N-(1-pentylpentylhexyl)-1,5-dideoxy-1,5-imino-D-glucitol, tetrabutyrate; N-(1-butylbutyl)-1,5-dideoxy-1,5-imino-D-glucitol, tetrabutyrate; N-(7-methyloctyl-)-1,5-dideoxy-1,5-imino-D-glucitol, tetrabutyrate; N-(8-methylnonyl)-1,5-dideoxy-1,5-imino-D-glucitol, tetrabutyrate; N-(9-methyldecyl)-1,5-dideoxy-1,5-imino-D-glucitol, tetrabutyrate; N-(10-methylundecyl)-1,5-dideoxy-1,5-imino-D-glucitol, tetrabutyrate; N-(6-cyclohexylhexyl-)-1,5-dideoxy-1,5-imino-D-glucitol, tetrabutyrate; N-(4-cyclohexylbutyl)-1,5-dideoxy-1,5-imino-D-glucitol, tetrabutyrate; N-(2-cyclohexylethyl)-1,5-dideoxy-1,5-imino-D-glucitol, tetrabutyrate; N-(1-cyclohexylmethyl)-1,5-dideoxy-1,5-imino-D-glucitol, tetrabutyrate; N-(1-phenylmethyl)-1,5-dideoxy-1,5-imino-D-glucitol, tetrabutyrate; N-(3-phenylpropyl)-1,5-dideoxy-1,5-imino-D-glucitol, tetrabutyrate; N-(3-(4-methyl)-phenylpropyl)-1,5-dideoxy-1,5-imino-D-glucitol, tetrabutyrate; N-(6-phenylhexyl)-1,5-dideoxy-1,5-imino-D-glucitol, tetrabutyrate; and mixtures of any two or more thereof. Diseases and conditions, for which N-substituted deoxynojirimycins may be effective, are disclosed in U.S. Pat. Nos. 4,849,430; 4,876,268; 5,411,970; 5,472,969; 5,643,888; 6,225,325; 6,465,487; 6,465,488; 6,515,028; 6,689,759; 6,809,083; 6,583,158; 6589,964; 6,599,919; 6,916,829; 7,141,582, U.S. patent applications Nos. 12/656,993 filed Feb. 22, 2010, 12/656,992 filed Feb. 22, 2010; U.S. provisional patent applications Nos. 61/282,507 filed Feb. 22, 2010, 61/272,253 filed Sep. 4, 2009, 61/272,252 filed Sep. 4, 2009, 61/186,614 filed Jun. 12, 2009, 61/282,508 filed Feb. 22, 2010; 61/272,254 filed Sep. 4, 2009. The diseases and conditions, for which N-substituted deoxynojirimycins may be effective, include, but not limited to HIV infection; Hepatitis infections, including Hepatitis C and Hepatitis B infections; lysosomal lipid storage diseases including Tay-Sachs disease, Gaucher disease, Krabbe disease and Fabry disease; and cystic fibrosis. The diseases and conditions, for which N-substituted deoxynojirimycins may be effective also included viral infections caused by or associated with a Dengue virus; viral infections caused by or associated with belonging to the Arenaviridae family, such as Pichinde virus or Junin virus; viral infections caused by or associated with belonging to the Poxyiridae family, such as Vaccinia virus; viral infections caused by or associated with belonging to the Filoviridae family, such as Ebola virus and Marburg virus; viral infections caused by or associated with belonging to the Bunyaviridae family, such as Rift Valley fever virus; viral infections caused by or associated with belonging to the Togaviridae family, such as Chikungunya virus and Venezuelan equine encephalitis virus; viral infections caused by or associated with belonging to the Orthomyxoviridae family, such as Influenza A virus, including H1N1 and H3N2 subtypes.

In some embodiments, the α-glucosidase inhibitor can be N-oxaalkylated deoxynojirimycins or N-alkyloxy deoxynojirimycin, such as N-hydroxyethyl DNJ (Miglitol or Glyset®) described in U.S. Pat. No. 4,639,436.

In some embodiments, the α-glucosidase inhibitor can be a castanospermines and/or a castanospermine derivative, such as a compounds of Formula (I) and pharmaceutically acceptable salts thereof disclosed in US patent application no. 2006/0194835, including 6-O-butanoyl castanospermine (celgosivir), and compounds and pharmaceutically acceptable salt thereof of Formula II disclosed in PCT publication no. WO01054692.

Diseases and conditions, for which castanospermine and its derivatives can be effective, are disclosed, in U.S. Pat. Nos. 4,792,558; 4,837,237; 4,925,796; 4,952,585; 5,004,746; 5,214,050; 5,264,356; 5,385,911; 5,643,888; 5,691,346; 5,750,648; 5,837,709; 5,908,867; 6,136,820; 6,583,158; 6,589,964; 6,656,912 and U.S. publications 20020006909; 20020188011; 20060093577; 20060194835; 20080131398. The diseases and conditions, for which castanospermine and its derivatives can be effective, include, but not limited, retroviral infections including HIV infection; celebral malaria; hepatitis infections including Hepatitis B and Hepatitis C infections; diabetes and lysosomal storage disorders.

In some embodiments, the alpha glucosidase inhibitor can be acarbose (O-4,6-dideoxy-4-[[(1S,4R,5S,6S)-4,5,6-trihydroxy-3-(hydroxymethyl)-2-cyc-lohexen-1-yl]amino]-α-D-glucopyranosyl-(1→4)-O-→-D-gluc-opyranosyl-(1→4)-D-glucose), or Precose®. Acarbose is disclosed in U.S. Pat. No. 4,904,769. In some embodiments, the alpha glucosidase inhibitor can be a highly purified form of acarbose (see, e.g., U.S. Pat. No. 4,904,769).

In some embodiments, the agent encapsulated inside the liposome can be an ion channel inhibitor. In some embodiments, the ion channel inhibitor can be an agent inhibiting the activity of HCV p7 protein. Ion channel inhibitors and methods of identifying them are detailed in US patent publication 2004/0110795. Suitable ion channel inhibitors include compounds of Formula I and pharmaceutically acceptable salts thereof, including N-(7-oxa-nonyl)-1,5,6-trideoxy-1,5-imino-D-galactitol (N-7-oxa-nonyl 6-MeDGJ or UT231B) and N-10-oxaundecul-6-MeDGJ. Suitable ion channel inhibitors also include, but not limited to, N-nonyl deoxynojirimycin, N-nonyl deoxynogalactonojirimycin and N-oxanonyl deoxynogalactonojirimycin.

In some embodiments, the agent encapsulated inside the liposome can be an iminosugar. Suitable iminosugars include both naturally occurring iminosugars and synthetic iminosugars. In some embodiments, the iminosugar can be deoxynojirimycin or N-substituted deoxynojirimycin derivative. Examples of suitable N-substituted deoxynojirimycin derivatives include, but not limited to, compounds of Formula II of the present application, compounds of Formula I of U.S. Pat. No. 6,545,021 and N-oxaalkylated deoxynojirimycins, such as N-hydroxyethyl DNJ (Miglitol or Glysetk®) described in U.S. Pat. No. 4,639,436.

In some embodiments, the iminosugar can be castanospermine or castanospermine derivative. Suitable castanospermine derivatives include, but not limited to, compounds of Formula (I) and pharmaceutically acceptable salts thereof disclosed in US patent application No. 2006/0194835 and compounds and pharmaceutically acceptable salt thereof of Formula II disclosed in PCT publication No. WO01054692.

In some embodiments, the iminosugar can be deoxynogalactojirimycin or N-substituted derivative thereof such as those disclosed in PCT publications No. WO99/24401 and WO01/10429. Examples of suitable N-substituted deoxynogalactojirimycin derivatives include, but not limited to, N-alkylated deoxynogalactojirimycins (N-alkyl-1,5-dideoxy-1,5-imino-D-galactitols), such as N-nonyl deoxynogalactojirimycin, and N-oxa-alkylated deoxynogalactojirimycins (N-oxa-alkyl-1,5-dideoxy-1,5-imino-D-galactitols), such as N-7-oxanonyl deoxynogalactojirimycin.

In some embodiments, the iminosugar can be N-substituted 1,5,6-trideoxy-1,5-imino-D-galactitol (N-substituted MeDGJ) including, but not limited to compounds of Formula II:

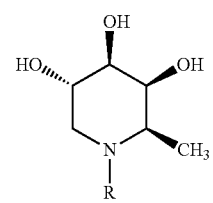

wherein R is selected from substituted or unsubstituted alkyl groups, substituted or unsubstituted cycloalkyl groups, substituted or unsubstituted heterocyclyl groups, or substituted or unsubstituted oxaalkyl groups. In some embodiments, substituted or unsubstituted alkyl groups and/or substituted or unsubstituted oxaalkyl groups comprise from 1 to 16 carbon atoms, or from 4 to 12 carbon atoms or from 8 to 10 carbon atoms. In some embodiments, substituted or unsubstituted alkyl groups and/or substituted or unsubstituted oxaalkyl groups comprise from 1 to 4 oxygen atoms, and from 1 to 2 oxygen atoms in other embodiments. In other embodiments, substituted or unsubstituted alkyl groups and/or substituted or unsubstituted oxaalkyl groups comprise from 1 to 16 carbon atoms and from 1 to 4 oxygen atoms. Thus, in some embodiments, R is selected from, but is not limited to —$(CH_2)_6$OCH$_3$, —$(CH_2)_6$OCH$_2$CH$_3$, —$(CH_2)_6$—O—$(CH_2)_2$CH$_3$, —$(CH_2)_6$—O—$(CH_2)_3$CH$_3$, —$(CH_2)_2$—O—$(CH_2)_5$CH$_3$, —$(CH_2)_2$—O—$(CH_2)_6$CH$_3$, and —$(CH_2)_2$—O—$(CH_2)_7$CH$_3$. N-substituted MeDGJs are disclosed, for example, in PCT publication No. WO01/10429.

In some embodiments, the agent encapsulated inside the liposome can include a nitrogen containing compound having formula III or a pharmaceutically acceptable salt thereof:

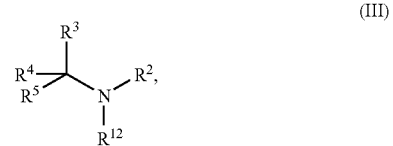

wherein $R^{12}$ is an alkyl such as $C_1$-$C_{20}$, or $C_1$-$C_6$ or $C_7$-$C_{12}$ or $C_8$-$C_{16}$ and can also contain from 1 to 5 or from 1 to 3 or from 1 to 2 oxygen, $R^{12}$ can be an oxa-substituted alkyl derivative. Examples if oxa-substituted alkyl derivatives include 3-oxanonyl, 3-oxadecyl, 7-oxanonyl and 7-oxadecyl.

$R^2$ is hydrogen, $R^3$ is carboxy, or a $C_1$-$C_4$ alkoxycarbonyl, or $R^2$ and $R^3$, together are

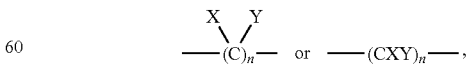

wherein n is 3 or 4, each X, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, or an aroyloxy, and each Y, independently, is hydrogen, hydroxy, amino, carboxy, a $C_1$-$C_4$ alkylcarboxy, a $C_1$-$C_4$ alkyl, a $C_1$-$C_4$ alkoxy, a $C_1$-$C_4$ hydroxyalkyl, a $C_1$-$C_6$ acyloxy, an aroyloxy, or deleted (i.e. not present);

$R^4$ is hydrogen or deleted (i.e. not present); and $R^5$ is hydrogen, hydroxy, amino, a substituted amino, carboxy, an alkoxycarbonyl, an aminocarbonyl, an alkyl, an aryl, an aralkyl, an alkoxy, a hydroxyalkyl, an acyloxy, or an aroyloxy, or $R^3$ and $R^5$, together, form a phenyl and $R^4$ is deleted (i.e. not present).

In some embodiments, the nitrogen containing compound has the formula:

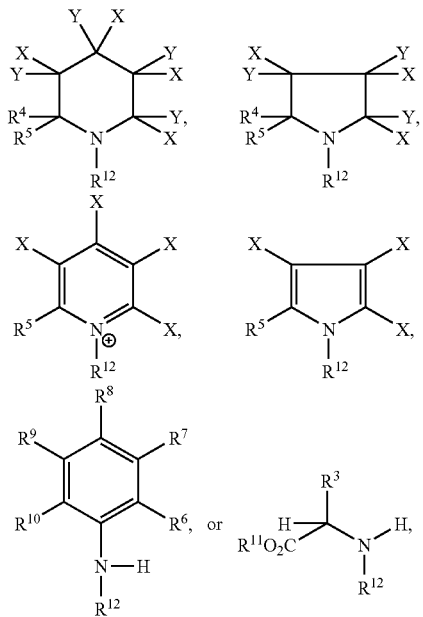

where each of $R^6$-$R^{10}$, independently, is selected from the group consisting of hydrogen, hydroxy, amino, carboxy, $C_1$-$C_4$ alkylcarboxy, $C_1$-$C_4$ alkyl, $C_1$-$C_4$ alkoxy, $C_1$-$C_4$ hydroxyalkyl, $C_1$-$C_4$ acyloxy, and aroyloxy; and $R^{11}$ is hydrogen or $C_1$-$C_6$ alkyl.

The nitrogen-containing compound can be N-alkylated piperidine, N-oxa-alkylated piperidine, N-alkylated pyrrolidine, N-oxa-alkylated pyrrolidine, N-alkylated phenylamine, N-oxa-alkylated phenylamine, N-alkylated pyridine, N-oxa-alkylated pyridine, N-alkylated pyrrole, N-oxa-alkylated pyrrole, N-alkylated amino acid, or N-oxa-alkylated amino acid. In certain embodiments, the N-alkylated piperidine, N-oxa-alkylated piperidine, N-alkylated pyrrolidine, or N-oxa-alkylated pyrrolidine compound can be an iminosugar. For example, in some embodiments, the nitrogen-containing compound can be N-alkyl-1,5-dideoxy-1,5-imino-D-galactitol (N-alkyl-DGJ) or N-oxa-alkyl-1,5-dideoxy-1,5-imino-D-galactitol (N-oxa-alkyl-DGJ) having the formula:

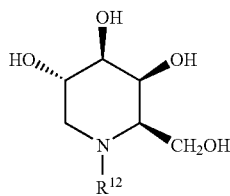

or N-alkyl-1,5,6-trideoxy-1,5-imino-D-galactitol (N-alkyl-MeDGJ) or N-oxa-alkyl-1,5,6-trideoxy-1,5-imino-D-galactitol having (N-oxa-alkyl-MeDGJ) having the formula:

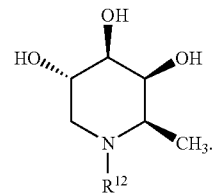

As used herein, the groups have the following characteristics, unless the number of carbon atoms is specified otherwise. Alkyl groups have from 1 to 20 carbon atoms and are linear or branched, substituted or unsubstituted. Alkoxy groups have from 1 to 16 carbon atoms, and are linear or branched, substituted or unsubstituted. Alkoxycarbonyl groups are ester groups having from 2 to 16 carbon atoms. Alkenyloxy groups have from 2 to 16 carbon atoms, from 1 to 6 double bonds, and are linear or branched, substituted or unsubstituted. Alkynyloxy groups have from 2 to 16 carbon atoms, from 1 to 3 triple bonds, and are linear or branched, substituted or unsubstituted. Aryl groups have from 6 to 14 carbon atoms (e.g., phenyl groups) and are substituted or unsubstituted. Aralkyloxy (e.g., benzyloxy) and aroyloxy (e.g., benzoyloxy) groups have from 7 to 15 carbon atoms and are substituted or unsubstituted.

Amino groups can be primary, secondary, tertiary, or quaternary amino groups (i.e., substituted amino groups). Aminocarbonyl groups are amido groups (e.g., substituted amido groups) having from 1 to 32 carbon atoms. Substituted groups can include a substituent selected from the group consisting of halogen, hydroxy, $C_{1-10}$ alkyl, $C_{2-10}$ alkenyl, $C_{1-10}$ acyl, or $C_{1-10}$ alkoxy.

The N-alkylated amino acid can be an N-alkylated naturally occurring amino acid, such as an N-alkylated α-amino acid. A naturally occurring amino acid is one of the 20 common α-amino acids (Gly, Ala, Val, Leu, Ile, Ser, Thr, Asp, Asn, Lys, Glu, Gln, Arg, His, Phe, Cys, Tip, Tyr, Met, and Pro), and other amino acids that are natural products, such as norleucine, ethylglycine, ornithine, methylbutenyl-methylthreonine, and phenylglycine. Examples of amino acid side chains (e.g., $R^5$) include H (glycine), methyl (alanine), —$CH_2C(O)NH_2$ (asparagine), —$CH_2$—SH (cysteine), and —$CH(OH)CH_3$ (threonine).

An N-alkylated compound can be prepared by reductive alkylation of an amino (or imino) compound. For example, the amino or imino compound can be exposed to an aldehyde, along with a reducing agent (e.g., sodium cyanoborohydride) to N-alkylate the amine. Similarly, a N-oxa-alkylated compound can be prepared by reductive alkylation of an amino (or imino) compound. For example, the amino or imino compound can be exposed to an oxa-aldehyde, along with a reducing agent (e.g., sodium cyanoborohydride) to N-oxa-alkylate the amine.

The nitrogen-containing compound can include one or more protecting groups. Various protecting groups are well known. In general, the species of protecting group is not critical, provided that it is stable to the conditions of any subsequent reaction(s) on other positions of the compound and can be removed at the appropriate point without adversely affecting the remainder of the molecule. In addition, a protecting group may be substituted for another after substantive synthetic transformations are complete. Clearly, where a compound differs from a compound disclosed herein only in that one or more protecting groups of the disclosed compound has been substituted with a different protecting group, that compound is within the invention. Further examples and conditions are found in Greene, *Protective Groups in Organic Chemistry*, (1st Ed., 1981, Greene & Wuts, 2nd Ed., 1991).

The nitrogen-containing compound can be purified, for example, by crystallization or chromatographic methods. The compound can be prepared stereospecifically using a stereospecific amino or imino compound as a starting material.

The amino and imino compounds used as starting materials in the preparation of the long chain N-alkylated compounds are commercially available (Sigma, St. Louis, Mo.; Cambridge Research Biochemicals, Norwich, Cheshire, United Kingdom; Toronto Research Chemicals, Ontario, Canada) or can be prepared by known synthetic methods. For example, the compounds can be N-alkylated imino sugar compounds or oxa-substituted derivatives thereof. The imino sugar can be, for example, deoxygalactonojirmycin (DGJ), 1-methyl-deoxygalactonojirimycin (MeDGJ), deoxynorjirimycin (DNJ), altrostatin, 2R,5R-dihydroxymethyl-3R,4R-dihydroxypyrrolidine (DMDP), or derivatives, enantiomers, or stereoisomers thereof.

In some embodiments, the agent encapsulated inside the lipid particle may be a compound of Formula IV or V:

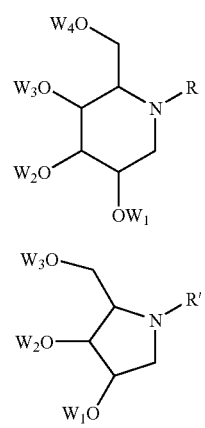

wherein R is:

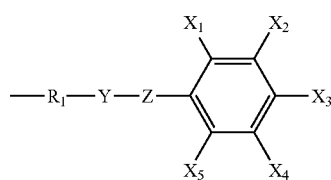

R' is:

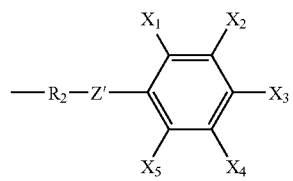

$R_1$ is a substituted or unsubstituted alkyl group; $R_2$ is a substituted or unsubstituted alkyl group; $W_{1-4}$ are independently selected from hydrogen, substituted or unsubstituted alkyl groups, substituted or unsubstituted haloalkyl groups, substituted or unsubstituted alkanoyl groups, substituted or unsubstituted aroyl groups, or substituted or unsubstituted haloalkanoyl groups; $X_{1-5}$ are independently selected from H, $NO_2$, $N_3$, or $NH_2$; Y is absent or is a substituted or unsubstituted $C_1$-alkyl group, other than carbonyl; Z is selected from a bond or NH; provided that when Z is a bond, Y is absent, and provided that when Z is NH, Y is a substituted or unsubstituted $C_1$-alkyl group, other than carbonyl; and Z' is a bond or NH. Compounds of formula IV and V and methods of their synthesis are disclosed, for example, in U.S. publication No. US2007/0275998. Non-limiting examples of compounds of Formula IV and V include N—(N'-{4'azido-2'-nitrophenyl)-6-aminohexyl)-deoxynojirimycin (NAP-DNJ) and N—(N'-{2,4-dinitrophenyl)-6-aminohexyl)-deoxynojirimycin (NDP-DNJ).

The syntheses of a variety of iminosugar compounds have been described. For example, methods of synthesizing DNJ derivatives are known and are described, for example, in U.S. Pat. Nos. 5,622,972, 5,401,645, 5,200,523, 5,043,273, 4,994,572, 4,246,345, 4,266,025, 4,405,714, and 4,806,650. Methods of synthesizing other iminosugar derivatives are known and are described, for example, in U.S. Pat. Nos. 4,861,892, 4,894,388, 4,910,310, 4,996,329, 5,011,929, 5,013,842, 5,017,704, 5,580,884, 5,286,877, and 5,100,797 and PCT publication No. WO 01/10429. The enantiospecific synthesis of 2R,5R-dihydroxymethyl-3R,4R-dihydroxypyrrolidine (DMDP) is described by Fleet & Smith (*Tetrahedron Lett.* 26:1469-1472, 1985).

The imaging agent can be a tagged or fluorescent aqueous material, such as calcein, or fluorescently labeled molecules such as siRNA, antibodies, or other small molecule inhibitors. Tagged lipophilic material can also be incorporated into lipid particles for incorporation into cellular membranes, such as the rh-PE lipid used for visualizing liposomes in cells and other similar lipids with tags for visualization or purification. This can also include tagged lipophilic proteins or drugs with fluorescent moieties or other tags for visualization or purification.

In some embodiments, the encapsulated active agent may be an retroviral agent, which may be, for example, nucleoside Reverse Transcriptase (RT) inhibitor, such as (−)-2'-deoxy-3'-thiocytidine-5'-triphosphate (3TC); (−)-cis-5-fluoro-1-[2-(hydroxy-methyl)-[1,3-oxathiolan-5-yl]cytosine (FTC); 3'-azido-3'-deoxythymidine (AZT) and dideoxy-inosine (ddI); a non-nucleoside RT inhibitors, such as N11-cyclopropyl-4-methyl-5,11-dihydro-6H-dipyrido[3,2-b:2'3'-e]-[1,4]diazepin-6-one (Neviparine), a protease inhibitor or a combination thereof.

Intercalated Moieties

In some embodiments, the lipid particle may comprise one or more moieties intercalated into its lipid layer or bilayer. Examples of intercalated moieties include, but not limited to, a transmembrane protein, a protein lipid conjugate, a labeled lipid, a lipophilic compound or any combination thereof. In some embodiments, the intercalated moiety may include a lipid-PEG conjugate. Such a conjugate may increase the in vivo stability of the lipid particle and/or increase its circulation time. In some embodiments, the intercalated moiety may include a long alkyl chain iminosugar, such as C7-C16 alkyl or oxaalkyl substituted N-deoxynojrimycin (DNJ) or C7-C16 alkyl or oxaalkyl substituted deoxygalactonojirimycin (DGJ). Non-limiting examples of long alkyl chain iminosugars include N-nonyl DNJ and N-nonyl DGJ. In some embodiments, the intercalated moiety may include a fluorophorelipid conjugate, which may be used for labeling the ER membrane of a cell contacted with the lipid bilayer particle. Such labeling may be useful for live and/or fixed-cell imaging in eukaryotic cells. The use of lipid particles may result in delivery of the intercalated moiety into the ER membrane of a cell.

Applications

The lipid particles that are capable of cholesterol inhibition may be used directly for treating and/or preventing a disease or condition caused by or associated with an increased cholesterol level. Examples of such diseases/conditions include but not limited to atherosclerosis and coronary artery disease. In some embodiments, the lipid particles that are capable of cholesterol inhibition may be used treating or preventing caused by or associated with an increased cholesterol level in a subject infected with an immunodeficiency virus, which can be a human infected with an HIV. The increased cholesterol level in such a subject may be a result of the infection. As immunodeficiency infections can be associated with accumulation of cellular cholesterol, and thereby leading to the development of atherosclerosis and/or CAD, lipid particles can target the immunodeficiency virus infected cells via a targeting molecule. In certain embodiments, the lipid particles may encapsulate one or more antiretroviral agent. Such lipid particles may deliver the antiretroviral agent to the immunodeficiency virus infected cells and simultaneously lower levels of cellular cholesterol, preventing atherosclerosis and/or CAD.

The lipid particle that are capable of cholesterol inhibition may be used for treating and/or preventing a disease or condition that is caused by or associated with a virus that relies on cholesterol for its replication. In certain cases, the disease or condition may be a viral infection. Examples of such viruses include, but not limited to, herpes simplex virus, influenza virus, murine leukemia virus, vaccinia virus, polyoma virus, Epstein-Barr virus, Semiliki Forest virus, Ebola virus, Marburg virus, dengue virus, measles virus, HIV, hepatitis C virus and hepatitis B virus. When used for a disease or condition that is caused by or associated with a virus, the lipid particles may contain one or more antiviral agents against the virus. Alternatively, the lipid particles may be used directly as a drug or prodrug by acting as a morphogenesis inhibitor of such viruses as HCV.

Administering

The composition comprising the lipid particles may administered to a subject with a goal of reducing cellular cholesterol in the subject. The initial level of cholesterol, prior to this administering may be normal or increased.

In some embodiments, the subject may be a cell. The composition comprising lipid particles may lower a level of cellular cholesterol in various cell types including but not limited to peripheral blood mononuclear cells (PBMCs), which includes macrophages, and a human hepatoma cell line, such as Huh7.5 cells.

In some cases, the cell may be a cell infected with a virus, which can be a virus that relies on cholesterol for its replication. In such a case the cholesterol inhibition by the lipid particles may lead to inhibition of viral replication, inhibition of viral assembly and secretion, production of non-infection viral particles with a decreased cholesterol level in the viral envelope and/or mis-localization of cellular receptors on the cell surface for virus entry. In some embodiments, the composition comprising lipid particles may be administered to a warm blooded animal, such as a mammal or a bird. In many cases, the subject can be a human. In some embodiments, the composition comprising the lipid particles may be administered by intravenous injection. Yet in some embodiments, the composition comprising the lipid particles can be administered via a parenteral routes other than intravenous injection, such as intraperitoneal, subcutaneous, intradermal, intraepidermal, intramuscular or transdermal route. Yet in some embodiments, the composition comprising the lipid particles can be administered via a mucosal surface, e.g. an ocular, intranasal, pulmonary, intestinal, rectal and urinary tract surfaces. Administration routes for lipid containing compositions, such as liposomal compositions, are disclosed, for example, in A. S. Ulrich, Biophysical Aspects of Using Liposomes as Delivery Vehicles, Bioscience Reports, Volume 22, Issue 2, April 2002, 129-150.

In certain cases, subcutaneous injections of lipid particles may preferred because such administering may lead to accumulation of the lipid particles within macrophages, thereby preventing the development of foam cells and therefore the early stages of atherosclerosis. The invention is further illustrated by, though in no way limited to, the following examples.

EXAMPLE

A proteomic analysis of cells treated with liposomes, that are efficient carriers of small water soluble molecules into the intracellular compartments of target cells, has shown that treatment leads to the downregulation of a key enzyme involved in cellular cholesterol biosynthesis, 3-hydroxy-3-methylglutaryl (HMG)-CoA synthase. Further experiments have shown that this downregulation may lead to decreased cholesterol levels, both free and esterified, within treated cells. Since the early stages of atherosclerosis and coronary artery disease begin with the formation of foam cells, which are cholesterol-laden macrophages, and because liposomes accumulate within macrophages following, for example, subcutaneous injections, liposome treatment may be a new, targeted treatment for these diseases. Furthermore, many viruses have been shown to be dependent on normal to increased cellular cholesterol levels, therefore the combination of decreased cholesterol levels in addition to the efficient delivery of antiviral drugs to target cells may be a novel, more effective antiviral therapy.

1. Liposome Preparation 1.1. Methodology for Liposome Preparation

Liposomes were prepared fresh for all assays described. Chloroform solutions of lipids were placed into glass tubes and the solvent was evaporated under a stream of nitrogen gas. Unless stated otherwise, lipid films were hydrated by vortexing in 1×PBS buffer to a final lipid concentration of 5 mM. The resulting multilamellar vesicles were extruded 11 times through a polycarbonate filter of 100 nm pore diameter using a Mini-Extruder device. Liposomes were filter sterilized using a 0.22 μm filter unit. FIGS. 2A-F illustrate lipids used in these studies: A. 22:6 PE; B. 22:6 PC; C. PI; D. PS; E. DOPE; F. CHEMS.

2. Decrease in HMG CoA Synthase (HMGCS) Protein in Cells Treated with Polyunsaturated ER Liposomes Cells treated with both pH-sensitive (i.e. liposomes comprising PE and CHEMS lipids but not containing PI or PS lipids) and ER liposomes (i.e. liposomes comprising PE lipids and at least one of PI or PS lipids) for 5 days were used for proteomic analysis to determine the increase or decrease of all detectable proteins in the cell. One protein decreased as a result of both pH-sensitive and ER-targeting liposome treatment was the enzyme HMG-CoA synthase (HMGCS). HMGCS catalyzes the first step in the mevalonate-isoprenoid pathway which is the synthesis of HMG-CoA from acetyl-CoA through acetoacetylCoA. To determine if 22:6 polyunsaturated (pu) ER liposome-treatment of Huh7.5 cells leads to a similar reduction in this enzyme, cells were treated with various concentrations of liposomes for 4 days prior to total cell lysis and analysis by Western blot to specifically identify HMGCS.

2.1. Methodology for Identifying HMGCS and Actin by Western Blot

Following treatments with puER liposomes (22:6 PE: 22:6 PC:PI:PS, 1.5:1.5:1:1) at final concentrations in the medium ranging from 1 μM to 100 μM, Huh7.5 cells were washed twice in 1×PBS, and resuspended in 1×PBS/1% Triton X-100 to a final protein concentration of 1 mg/ml. Protein concentration was determined by Bradford Assay (Bio-Rad) using a BSA standard. SDS-PAGE was performed by loading 10 μg of protein per well in 4-12% bis-tris NuPAGE gels (Invitrogen), and separated using the NuPAGE MES SDS buffer following manufacturer's recommendations. Protein was transferred to nitrocellulose membranes and immunoblotting was carried out using the WesternBreeze® anti-goat AP chemiluminescent kit (Invitrogen) with primary goat anti-human HMGCoA synthase and anti-human actin antibodies (Santa Cruz) diluted 1:100, following the manufacturer's protocol.

2.2. Downregulation of HMGCS with puER Liposome Treatment

Figure 3:
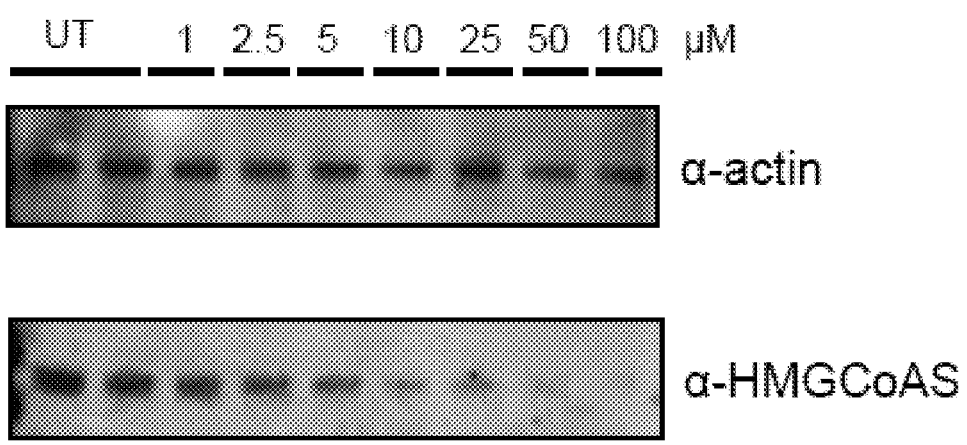

As shown with ER liposomes composed of mainly 18:1 lipids (18:1 PE:18:1 PC:PI:PS, 1.5:1.7:1.5:0.3), treatment with 22:6 ER liposomes also decreased the amount of HMG-CoA-synthase in a dose-dependent manner (FIG. 3).

FIG. 3 shows results of Western blot analysis of 22:6 ER liposome-treated, JC-1-infected Huh7.5 cells (MOI=0.5) using both anti-actin and anti-HMGCS antibodies. Cells were treated with 22:6 ER liposomes at various concentrations for 4 days, at which point cells were harvested and disrupted by resuspension in 1% Triton X-100/1xPBS. Cell lysates were assayed for protein content, and 30 μg of total protein were loaded per well prior to separation by SDS-PAGE. A representative image from a single experiment is shown. The experiment was independently repeated three times.

3. Treatment of Cells with puER Liposomes Decreases Levels of Cellular Cholesterol Since liposome treatment has been shown to decrease levels of HMGCS in cells, assays to determine both free and esterified cholesterol levels in these cells were carried-out to quantify this inhibition in terms of inhibition of cholesterol biosynthesis. Total cholesterol and free cholesterol levels were quantified in 22:6 ER liposome and 22:6 PEG-ER liposome-treated Huh7.5 cells. Esterified cholesterol was determined by calculating the difference between total and free cholesterol values.

3.1. Method for Quantification of Total and Free Cholesterol Levels in Cells Following treatments, Huh7.5 cells or PBMCs were washed twice in 1×PBS, and resuspended in 1×PBS/1% Triton X-100 to a final protein concentration of 1 mg/ml. Protein concentration was determined by Bradford Assay (Bio-Rad) using a BSA standard. Cholesterol assays were performed on cellular lysates corresponding to 10 μg total protein. Total cholesterol and free cholesterol levels were quantified using the Amplex® Red cholesterol assay kit (Invitrogen) in either the presence or absence of cholesterol esterase, respectively, following the manufacturer's protocol.

3.2. Quantification of Total and Free Cholesterol Levels in Both Huh7.5 Cells and PBMCs Following Treatment with puER and PEGylated puER Liposomes Total cholesterol and free cholesterol levels were quantified in 22:6 ER liposome and 22:6 PEG-ER liposome-treated Huh7.5 cells. Esterified cholesterol was determined by calculating the difference between total and free cholesterol values. Results demonstrate a dose-dependent decrease in total cholesterol levels (FIG. 4), with PEG-ER liposome treatment having similar effects as the non-PEGylated composition, demonstrating that PEGylation does not affect the inhibition of cholesterol biosynthesis by ER liposomes. Total cholesterol levels are significantly lower (56%, SD=2.7%) in 50 μM 22:6 ER liposome treated samples compared to the untreated control, and the majority of this decrease may be due to lower levels of free cholesterol (47% of the untreated value, SD=2.5%) compared to esterified cholesterol (75% of the untreated value, SD=1.1%) within the cell.

Figure 4:
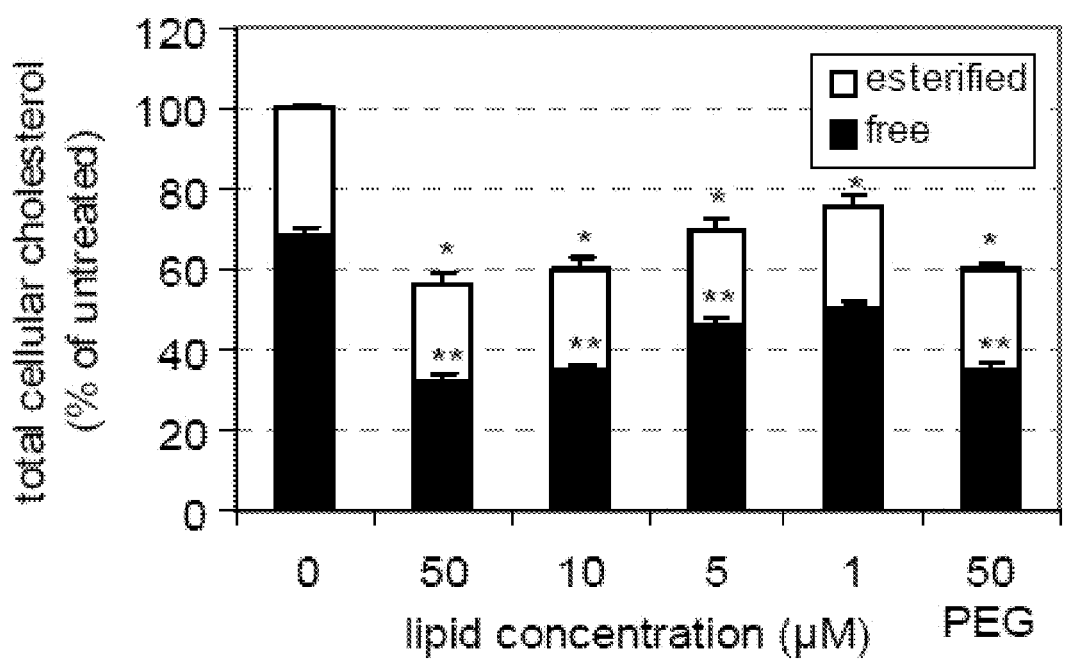

FIG. 4 shows results of quantification of both free and total cholesterol from 22:6 PE:22:6 PC:PI:PS-treated, JC1-infected Huh7.5 cells (MOI=0.5). Cells were treated for 4 days with liposomes at various concentrations, including a PEGylated version of 22:6 ER liposomes. Following the incubation, cells were harvested and disrupted with 1% Triton® X-100/1xPBS, and 10 μg of each sample was used for cholesterol assays both in the presence and absence of cholesterol esterase to quantify both total and free cholesterol in cells, respectively. Esterified cholesterol was calculated as the difference between the two values. Results represent the mean (and SD) of triplicate samples from three independent experiments. Data are presented in relation to the untreated controls (100%), and significant differences from this value are denoted with * ($P<0.05$) or ** ($P<0.001$).

Phytohemagglutinin (PHA)-stimulated PBMCs were incubated with 22:6 ER liposomes, and both free and esterified cholesterol levels were quantified following a 4 day incubation. As demonstrated in FIG. 5, untreated PBMCs contain 78% (SD=5.9%) free cholesterol and 22% (SD=3.8%) esterified cholesterol. Treatment with 50 μM 22:6 ER liposomes led to an overall decrease in cellular cholesterol of 28% (SD=6.5%). Free cholesterol levels were significantly lowered by 33% (SD=6.3%, $P<0.001$), but there was no significant decrease in esterified cholesterol at this concentration compared to the untreated control. PEGylated 22:6 ER liposomes also decreased free cholesterol levels by 29% (SD=3.9, $P<0.001$), with no significant effect on esterified cholesterol levels.

Figure 5:
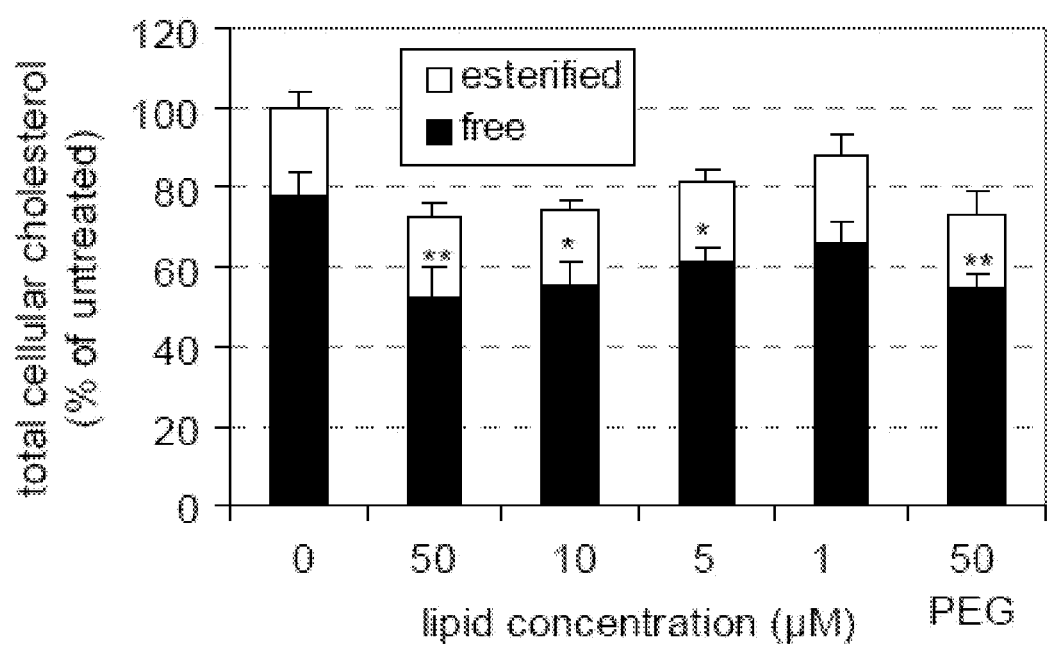

FIG. 5 demonstrate results of experiments for PHA-stimulated PBMCs treated with 22:6 ER liposomes for 4 days. Cells were then harvested and disrupted by resuspension in 1% Triton® X-100/1xPBS and 10 μg of each sample was used for cholesterol assays both in the presence and absence of cholesterol esterase to quantify both total and free cholesterol in cells, respectively. Esterified cholesterol was calculated as the difference between the two values. Data represent the mean and SD of triplicates of three independent experiments. All values are shown as a percentage in relation to the untreated control (100%), and significant differences from this value are denoted with * ($P<0.05$) or ** ($P<0.001$).

4. Decreased Intracellular Cholesterol has Antiviral Effects Against HCV

HCV has been shown to be dependent on levels of cellular cholesterol for efficient viral replication. Additionally, ER liposomes have been shown to be antiviral against HCV by competing with the virus for cellular receptors. To monitor the combined antiviral activities of puER liposomes and PEGylated puER liposomes against HCV, virus was cultured in the presence of liposomes for 16 days (4 rounds of 4 day treatments). Antiviral activity was monitored by quantifying the viral infection in cells, as well as viral secretion and the infectivity of secreted virions throughout the treatment. Levels of cellular cholesterol were also measured within treated cells.

4.1. Methodology for HCV Cell Culture and Quantification of Viral Infection and Secretion JC-1 HCV Cell Culture (HCVcc):

Viral stocks of known infectious titers (focus forming units (ffu)/ml) were used to infect naïve Huh7.5 cells in all assays described. For liposome treatment assays JC1-infected Huh7.5 cells were seeded into 6 well plates at a density of $3\times10^5$ cells/well in complete DMEM/10% FBS with or without liposomes in a total volume of 2 ml per well, and left to incubate 4 days. Following incubation, supernatant was harvested for HCV RNA quantification. Cells were washed once with 1×PBS, detached in 0.5% trypsin/EDTA (Invitrogen), counted, and frozen at −20° C. prior to further analysis. For assays with multiple passages, following cell counting with trypan blue, $3\times10^5$ cells were re-seeded into 6 well plates for another round of treatments as described.

Quantification of HCV by RT-PCR:

Virus secretion analysis was performed by quantitative PCR on viral RNA extracted from 500 µl of supernatant using the QIAGEN QIAamp® Viral RNA Purification Kit, following the manufacturers' protocol. 500 µl of supernatant were first concentrated to 140 µl using a Centricon® concentrator (10,000 KDa MW cut-off, Millipore). Quantification of secreted viral RNA was done by first converting isolated RNA to cDNA using a reverse transcriptase reaction (TaqMan®, ABI) with primer RC21 (5'-CTCCCGGGGCACTCG-CAAGC-3' (SEQ ID NO: 1)) followed by real-time PCR using a SyBr® Green mix (QIAGEN) and both RC21 and RC1 primers (5% ATGCCATGGCGTTAGTA-3' (SEQ ID NO: 2)) directed against the HCV cDNA. HCV transcript levels were determined relative to a standard curve comprised of serial dilutions of HCV JC-1 cDNA.

4.2. HCV Core Immunofluorescence for Measuring Viral Infectivity

The infectivity of secreted HCV virions within the supernatant of treated JC-1-infected Huh7.5 cells was determined by infecting naïve Huh7.5 cells. Naïve Huh7.5 cells were seeded at a density of $5\times10^4$ cells/well in a 48 well plate, and left to adhere overnight before medium was replaced with 200 µl of sample supernatant. Supernatant was left to infect naïve Huh7.5 cells for 1 h before cells were washed twice with 1×PBS and then incubated in 500 µl complete DMEM/10% FCS for 2 days. After the 2 day incubation, cells were washed twice with 1×PBS, fixed in methanol/acetone (1:1, vol/vol) for 10 min, and washed twice in 1×PBS/0.1% Tween®-20. Cells were then incubated for 1 h in 1×PBS/0.1% Tween®-20 containing 3 µg/ml mouse anti-HCV core antibody (Affinity BioReagents), washed twice in 1×PBS/0.1% Tween®-20, incubated 1 h in 1×PBS/0.1% Tween®-20/1:1000 FITC-labeled anti-mouse secondary antibody (Sigma), washed twice more, and stained with DAPI. Fluorescent images were taken using a Nikon Eclipse TE2000-U microscope. The percentage of infected cells is calculated by counting the total number of cells infected with HCV (detected by the anti-HCV antibody) divided by the total number of cells in the assay (detected by DAPI staining)

Figure 6:
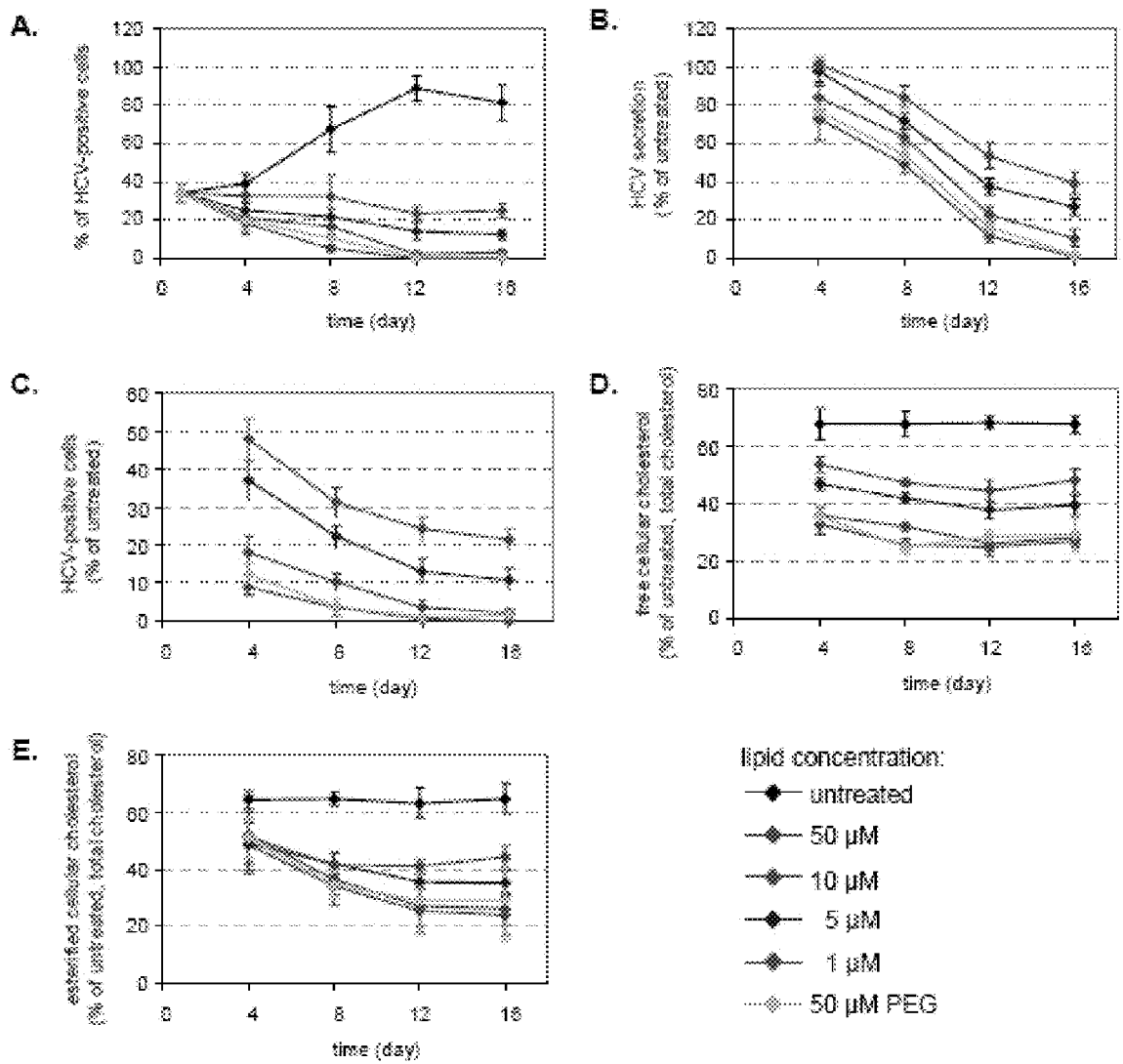

4.3. Long-Term Treatment of HCVcc-Infected Huh7.5 Cells with puER and PEGylated puER Liposomes JC-1 HCVcc-infected Huh7.5 cells were treated with ER liposomes over a period of 16 days (4 rounds of treatment). Every 4 days, cells were passaged into fresh media containing treatments and the viral infection in cells, HCVcc secretion, and infectivity of secreted particles were quantified. Cells were infected at MOI=0.02 and treatments were begun once infection level in cells reached 30%-40% of total cells (as determined by core protein immunofluorescence). FIG. 6a shows the HCVcc infection levels in cells over the 16 day treatment period with the different treatments of 22:6 ER liposomes. All liposome treatments prevented spread of the viral infection within Huh7.5 cells, and led to a dose-dependent decrease in the total number of infected cells following only 4 days of treatment. There were no infected cells observed in cultures following the 16 day treatment with 50 µM 22:6 ER liposomes. Results of HCV secretion (FIG. 6b) throughout the 16 day treatment demonstrate a similar pattern, where HCV secretion is decreased compared to the untreated samples in a dose-dependent manner. Following a single round of treatment, 22:6 ER liposomes were shown to significantly decrease HCV secretion by 27% (SD=11.3%) at a concentration of 50 µM; a similar decrease was observed with 50 µM 22:6 PEG-ER liposome-treatment (23%, SD=6.6%). Day 16 supernatant from 50 µM 22:6 ER liposome-treated cells when quantified by RT-PCR contained less than 1% of HCV RNA compared to the untreated sample. Although the present invention is not limited by any theories, this result may suggest that the infection may not have been cleared at this point (RNA levels were significantly higher than background levels); however, liposome treatment successfully reduced viral secretion by over 2 orders of magnitude. The infectivity of secreted viral particles was determined at each passage, and results are presented in FIG. 6c. The greatest effect of ER liposomes was on viral infectivity, which was reduced to zero (or to below any detectable limit) by day 16 treatment with 50 µM 22:6 ER liposomes. However, following only a single round of treatment 50 µM 22:6 ER liposomes decreased HCV infectivity by 91% (SD=2.2%). Even the lowest concentration of 22:6 ER liposomes tested, 1 µM, decreased infectivity by 52% (SD=5.3%), suggesting ER liposomes are potent inhibitors of viral infectivity.

Throughout the treatment period, levels of free cholesterol and esterified cholesterol were also quantified in the treated Huh7.5 cells (FIGS. 6d and 6e, respectively). Interestingly, although the levels of free cholesterol are lowered following only 1 round of treatment, this level does not significantly decrease further in subsequent rounds. Instead, a gradual dose-dependent decrease in esterified cholesterol was observed from day 4 to day 12 of treatment, at which point levels seem to plateau in all treatments. The normal ratio of free:esterified cholesterol in untreated cells is approximately 2:1 as detected by these assays, and although 50 µM 22:6 ER liposome treatment reduces this ratio to as low as 1.3:1 by day 4 of treatment, the 2:1 ratio is restored in all treated samples by day 12.

FIG. 6A-E show results of experiments for treatment of JC-1-infected Huh7.5 cells (MOI=0.02) with 22:6 ER liposomes for 16 days. (A) JC-1 HCVcc infection levels in Huh7.5 cells throughout treatment. (B) JC-1 HCVcc secretion. (C) Infectivity of secreted JC-1 HCVcc particles. (D) Free cholesterol levels in cells. (E) Esterified cholesterol in cells. Data represent the average of triplicate samples from two independent experiments. It has previously been demonstrated that a high level of virion-associated cholesterol is required for viral infectivity (Aizaki, Morikawa et al. 2008). Therefore, the decrease in viral infectivity as a result of ER liposome treatment may be a result of reduced cholesterol within the viral membrane of secreted particles. To test this possibility, HCVcc secreted from 50 µM 22:6 ER liposome-treated, 50 µM 22:6 PEG-ER liposome-treated and untreated cells were incubated with free cholesterol in an attempt to restore viral infectivity.

4.4. Methodology for Incubation of HCVcc with Free Cholesterol

The RNA of HCVcc particles secreted from untreated and 50 µM liposome-treated Huh7.5 cells following a 4 day incubation period was quantified by RT-PCR as previously described.

Samples were normalized by dilution in complete DMEM/10% FBS to the lowest concentration. HCVcc was incubated with free cholesterol (Sigma) for 1 h at 37° C. as previously described (Aizaki, Morikawa et al. 2008), and used to infect naïve Huh7.5 cells for HCV core protein immunofluorescence infectivity assays as described above.

Figure 7:
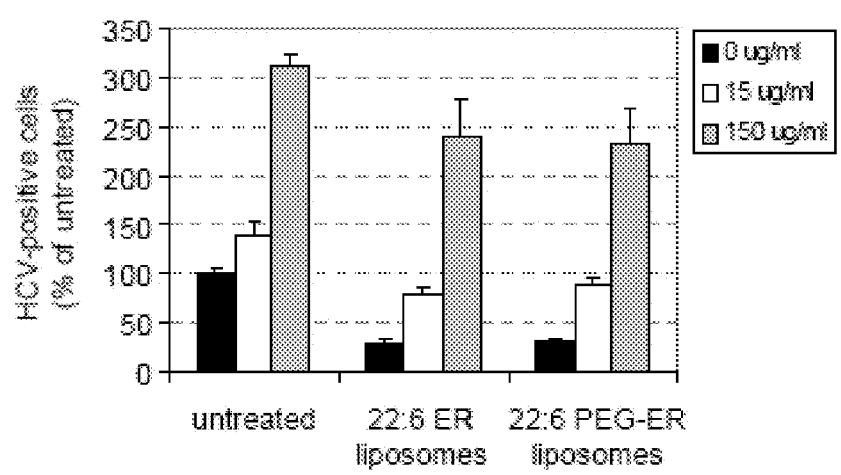

4.5. Results Following the Incubation of puER and PEGylated puER Liposome-Treated HCVcc with Free Cholesterol HCVcc secreted from 50 µM 22:6 ER liposome-treated, 50 µM 22:6 PEG-ER liposome-treated and untreated cells were quantified by RT-PCR and normalized to $2 \times 10^4$ RNA copies/ml. Normalized virus supernatants were pre-incubated with cholesterol at a final concentration of either 15 µg/ml, or 150 µg/ml, or left untreated for 1 h at 37° C. as previously described (Aizaki, Morikawa et al. 2008), and then were used to infect naïve Huh7.5 cells. As shown in FIG. 7, all HCVcc supernatants demonstrated increased infectivity when pre-incubated with exogenous cholesterol; however, at a concentration of 15 µg/ml cholesterol, HCVcc from ER liposome-treated cells led to a greater increase in viral infectivity when compared to untreated HCVcc (282% and 138% of the no cholesterol control, respectively). Although the addition of exogenous cholesterol to ER liposome-treated HCVcc restores a significant percentage of viral infectivity, the levels are not comparable to those observed with the untreated virions, which may suggest there may be possibly an additional defect within HCVcc particles secreted from ER liposome-treated cells that reduces viral infectivity. FIG. 7 shows Infectivity of 22:6 ER liposome-treated, PEGyated 22:6 ER liposome-treated and untreated JC-1 HCVcc treated with exogenous cholesterol (final concentrations of 15 µg/ml and 150 µg/ml cholesterol). Virus samples were taken from a 4 day incubation in the presence of liposomes, normalized to the lowest concentration of JC-1 RNA (determined by quantitative PCR), and pretreated with cholesterol for 1 h at 37° C. Following the addition of cholesterol, viral samples were used to infect naïve Huh7.5 cells and infectivity of these samples was quantified as previously described. Results represent the mean (and SD) of triplicate samples from three independent experiments.

Studies have also shown that decreasing levels of cellular cholesterol reduces the ability of HCVcc to infect cells (Aizaki, Morikawa et al. 2008). This effect may be likely due to the fact that both CD81 and SR-BI, two main cellular receptors for HCV, may require cholesterol in the form of lipid rafts in order to localize to the plasma membrane (Soldaini, Wack et al. 2003; Cherukuri, Shoham et al. 2004; Rhainds, Bourgeois et al. 2004), a process which may be required for HCV infection (Kapadia, Barth et al. 2007). To investigate whether ER liposomes may prevent HCVcc infection by decreasing levels of cellular cholesterol, naïve Huh7.5 cells were pre-treated with 22:6 ER liposomes for 4 days prior to infection with untreated JC-1 HCVcc.

4.6. Results Following Pre-Treatment of Huh7.5 Cells with puER and PEGylated puER Liposomes and Infection with HCVcc FIG. 8 confirms that ER liposome pre-treatment results in a dose-dependent decrease in the ability of HCVcc to infect naïve cells; the greatest effect is seen with 50 µM 22:6 ER liposome-treatment, where viral infection was decreased by 89% (SD=1.9%).

Figure 8:
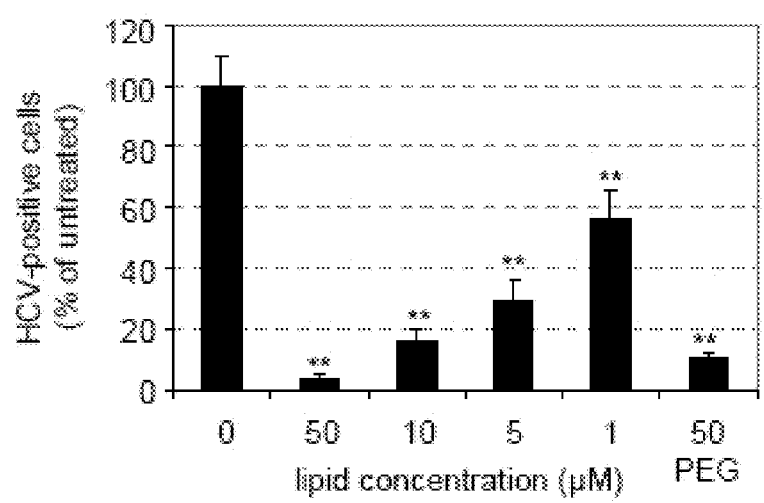

FIG. 8 shows results of experiments for uninfected Huh7.5 cells treated with 22:6 ER liposomes for 4 days prior to infection with JC-1 HCVcc (MOI=0.5). Viral infectivity was quantified as previously described. Results represent the mean (and SD) of triplicate samples from three independent experiments. Data are presented in relation to the untreated controls (100%), and significant differences from this value are denoted with * ($P<0.05$) or ** ($P<0.001$).

5. Decreased Intracellular Cholesterol has Antiviral Effects Against HIV

HIV has also been shown to be dependent on cellular cholesterol (lipid rafts) and viral-associated cholesterol for proper assembly and infectivity, respectively. To investigate whether ER liposomes could act as an HIV-1 antiviral, PBMCs were infected with 3 HIV-1 primary isolates (LAI, 93UG067, and 93RW024) at a $TCID_{50}=100$, and treatment with puER and PEGylated puER liposomes lasted 4 days following infection. HIV secretion and infectivity was quantified from cellular supernatant by p24 ELISA.

5.1. Methodology for Quantifying HIV Secretion and Infectivity Following Treatment with puER and PEGylated puER Liposomes HIV-1 Primary Isolate Cell Culture:
To infect cells, $4 \times 10^5$ PHA-activated PBMCs and 100 $TCID_{50}$ (tissue culture infectious dose 50%) of primary isolate stock were added to each well of a 96 well plate. Following an overnight incubation of 16 h, cells were washed three times with complete RPMI medium, and resuspended in complete RPMI/IL2 with or without liposomes. On day 5, supernatant containing HIV virions secreted from cells was collected and the p24 concentration was quantified for each by p24 capture ELISA.

Quantitative p24 ELISA:

HIV samples were inactivated with 1% Empigen (vol/vol) prior to p24 analysis. ELISAs to quantify p24 were carried out using the anti-p24 D7320 antibody (Aalto Bioreagents, Dublin, U.K.) to capture p24 from treated supernatant, and detected using the anti-p24 secondary antibody, BC1071-AP (Aalto Bioreagents), following the manufacturers' protocol. Alkaline phosphatase activity was measured using the AMPAK™ ELISA kit (Dako, Ely, U.K.) following the manufacturers' protocol. Samples were standardized using recombinant p24 protein (Aalto Bioreagents).

HIV Infectivity Assays:

The infectivity of HIV virions secreted from PBMCs treated with liposomes was determined using supernatant containing HIV virions secreted from liposome-treated cells. All supernatants were diluted to a final p24 concentration of 10 ng/ml in complete RPMI/IL2, and 100 µl was added to $4 \times 10^5$ PHA-activated PBMCs, also in 100 µl of medium, for a final p24 concentration of 5 ng/ml, and left to incubate overnight. The following day cells were washed as described, resuspended in 200 µl of fresh RPMI/IL2, and left to incubate 4 days before supernatant was collected and assayed for p24 content by capture ELISA.

5.2. Results Following Treatment of HIV-1-Infected PBMCs with puER and PEGylated puER Liposomes HIV secretion was quantified from cellular supernatant by p24 ELISA following a 4 day treatment and results demonstrate a dose-dependent decrease in both HIV secretion and the infectivity of secreted particles (FIGS. 9a and 9b, respectively). As shown with HCVcc, the major mechanism for antiviral activity may appear to be by decreasing the formation of infectious virions: it was observed a 50% (SD=4.6%) decrease in the infectivity of secreted HIV with 50 µM 22:6 ER liposome treatment, whereas there was only a 22% (SD=4.6%) decrease in viral secretion.

FIG. 9A shows average secretion of three genetically diverse primary isolates of HIV-1 (LAI, 93UG067, and 93RW024) during a 4 day treatment with 22:6 ER liposomes. HIV-1 secretion was measured by quantifying the HIV-1 p24 matrix protein using capture ELISA.

FIG. 9B shows infectivity of HIV-1 secreted from 22:6 ER liposome-treated PBMCs. The infectivity of secreted virions was determined by using the supernatant to infect naïve PBMCs, followed by p24 ELISA to monitor secretion following infection. Data represent the mean and SD of triplicates of three independent experiments. All values are shown as a percentage in relation to the untreated control (100%), and significant differences from this value are denoted with * (P<0.05) or ** (P<0.001).

6. Polyunsaturated ER Liposomes Compete with HCVcc for Binding to Cell Surface Lipoprotein Receptors The low-density lipoprotein receptor (LDLr) is a membrane glycoprotein that may control the primary pathway through which cholesterol enters the cells, via the clathrin-mediated endocytosis of VLDL-derived lipoprotein particles. LDLr is also a candidate HCV receptor based on the finding that HCV particles associate with lipoproteins and uptake of viral particles by cultured cells correlates with the expression of the LDLr. In order to see if liposomes use LDLr for uptake into cells, drugs which have been shown to up- and down-regulate the expression of LDLr in Huh7 cells, squalestatin and 25-hydroxycholesterol, respectively, were used to observe any effects on ER liposome uptake in Huh7.5 cells in the presence of a JC-1 HCVcc infection.

6.1. Methodology for Monitoring Liposome Uptake in the Presence of Drugs which Up- and Down-Regulate LDLr Expression in Huh7.5 Cells Liposomes were prepared as described in US patent publication no. 20090252785 and included 1% (total moles) of rh-PE for monitoring their uptake in cells. JC-1-infected (MOI=0.5) or uninfected Huh7.5 cells were seeded in 6 well plates at a density of $3 \times 10^5$ cell/well in 2 ml of complete DMEM/10% FCS medium. Cells were either pre-treated or not with 1 µM and 10 µM squalestatin (SQ, Sigma) or 25-hydroxycholesterol (25-HC, Sigma) for 24 h in serum-free complete DMEM. Following the 24 h pre-incubation, rh-labeled liposomes were added to a final lipid concentration of 50 µM, and left to incubate for a further 24 h. Following incubation times, cells were washed twice in 1×PBS, detached, counted, and resuspended in 200 µl 1×PBS/1% Triton® X-100 before being transferred to a 96 well plate to read in a spectrofluorometer at λex=550 nm, Xem=590 nm.

6.2. Results of Liposome Uptake into Huh7.5 Cells in the Presence of Squalestatin and 25-Hydroxycholesterol Cells were cultured in the presence of either SQ or 25-HC for 24 h (final concentrations of 10 µM and 1 µM for both) prior to the addition of rhodamine-labeled 22:6 ER liposomes for 24 h. Treatment of cells with 10 µM 25-HC led to a 69% (SD=4.9%) decrease in liposome uptake, whereas 10 µM SQ significantly increased liposome uptake to 117% (SD=10.7%), demonstrating a dependence on LDLr for uptake of ER liposomes into Huh7.5 cells (FIG. 10).

Figure 10:
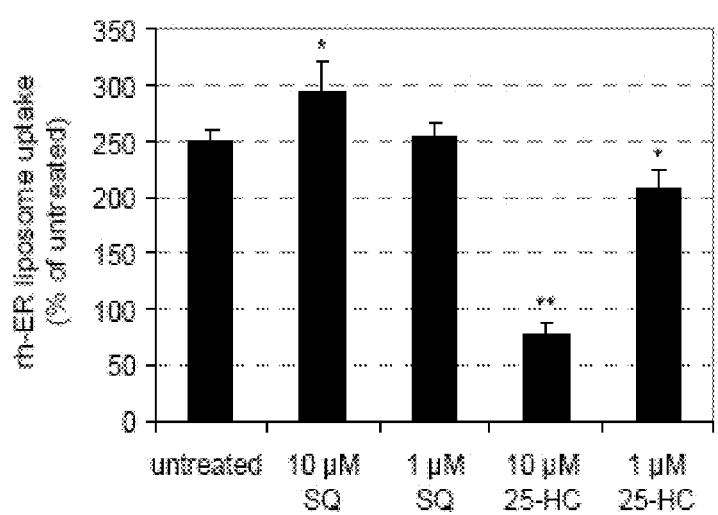
FIG. 10 shows results of experiments for uninfected Huh7.5 cells that were incubated in the presence of drugs used to upregulate and downregulate the expression of lipoprotein receptors (SQ and 25-HC, respectively) for 24 h in serum-free complete DMEM.

FIG. 10 shows results of experiments for uninfected Huh7.5 cells that were incubated in the presence of drugs used to upregulate and downregulate the expression of lipoprotein receptors (SQ and 25-HC, respectively) for 24 h in serum-free complete DMEM. 22:6 ER liposomes (final lipid concentration of 50 µM), labeled with 1% rh-PE in the lipid bilayer, were then added to cells and left to incubate a further 24 h. Cells were then harvested, counted, and rh-PE fluorescence was measured at λex=550 nm, Xem=590 nm. All data represent the mean and SD of triplicates from three independent experiments. Data are presented in relation to the untreated control (100%), and significant differences from this value are denoted with * (P<0.05) or ** (P<0.001).

Figure 11:
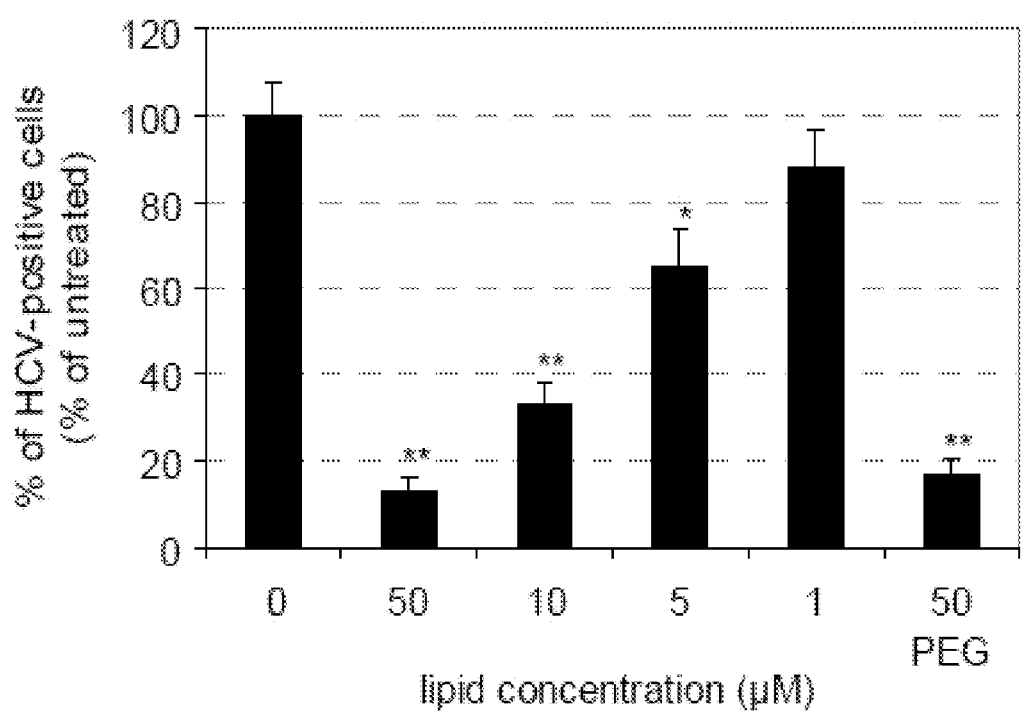
FIG. 11 shows results of experiments for addition of 22:6 puER liposomes to HCVcc viral stocks during the 1 hour infection of Huh7.5 cells.

Since HCV may be thought to use LDLr as a cellular receptor, ER liposomes may also reduce the infectivity of HCVcc by directly competing with the virus for cellular receptors necessary for internalization. To test this hypothesis, 22:6 ER liposomes were mixed with JC-1 HCVcc and used to the infect naïve Huh7.5 cells. Results demonstrate that ER liposomes can neutralize HCVcc infection of Huh7.5 by over 50% using lipid concentrations above 5 µM (FIG. 11). The greatest effect was seen with ER liposomes added to a final concentration of 50 µM, where viral infectivity was decreased by 87% (SD=2.9%). This experiment was repeated with a 1 h pre-incubation of virus and liposomes prior to addition to naïve cells for infection, and results are practically identical to those presented (data not shown). Although the present invention is not limited by any theory, this result may suggest that liposomes do not directly interact with HCVcc particles, but only with cellular receptors.

FIG. 11 shows results of experiments for addition of 22:6 puER liposomes to HCVcc viral stocks during the 1 hour infection of Huh7.5 cells. Liposomes were added to the viral stocks at various concentrations and used to infect naïve Huh7.5 cells. The ability of puER liposomes to neutralize the HCVcc infections was monitored by quantifying the number of infected cells following a 2 day incubation period using the HCV core protein immunofluorescence assay. All data represent the mean and SD of triplicates from three independent experiments. Data are presented in relation to the untreated control (100%), and significant differences from this value are denoted with * ($P<0.05$) or ** ($P<0.001$).

REFERENCES

Aiello, R. J., D. Brees, et al. (2002). *Arterioscler Thromb Vasc Biol.* 22(4): 630-637.
Aizaki, H., K.-J. Lee, et al. (2004). *Virology* 324(2): 450-461.
Aizaki, H., K. Morikawa, et al. (2008). *J Virol.* 82(12): 5715-5724.
Alfano, M., H. Schmidtmayerova, et al. (1999). *J Exp Med.* 190(5): 597-606.
Allred, K. F., E. J. Smart, et al. (2006). *J Biol Chem.* 281(3): 1419-1425.
Aloia, R. C., H. Tian, et al. (1993). *Proc Natl Acad Sci USA.* 90(11): 5181-5185.
Babitt, J., B. Trigatti, et al. (1997). *J Biol Chem.* 272(20): 13242-13249.
Bavari, S., C. M. Bosio, et al. (2002). *J Exp Med.* 195(5): 593-602.
Beer, C., L. Pedersen, et al. (2005). *Virol J.* 2(1): 36.
Bremer, C. M., C. Bung, et al. (2009). 11: 249-260.
Brown, M. S, and J. L. Goldstein (1999). *Proc Natl Acad Sci USA.* 96(20): 11041-11048.
Buhaescu, I. and H. Izzedine (2007). *Clin Biochem.* 40(9-10): 575-584.
Campbell, S. M., S. M. Crowe, et al. (2001). *J Clin Virol.* 22(3): 217-227.
Campbell, S. M., S. M. Crowe, et al. (2002). *AIDS* 16(17): 2253-2261.
Carpentier, A., B. W. Patterson, et al. (2005). *Atherosclerosis* 178(1): 165-172.
Charrin, S., S. Manié, et al. (2003). *Eur J Immunol.* 33(9): 2479-2489.
Chatterjee, P. K., C. H. Eng, et al. (2002). *J Virol.* 76(24): 12712-12722.
Cherukuri, A., T. Shoham, et al. (2004). *J Immunol.* 172(1): 370-380.
Chisari, F. V. (2005). *Nature* 436(7053): 930-932.
Chung, C.-S., C.-Y. Huang, et al. (2005). *J Virol.* 79(3): 1623-1634.
del Real, G., S. Jimenez-Baranda, et al. (2004). *J Exp Med.* 200(4): 541-547.
Dhaliwal, B. S, and U. P. Steinbrecher (2000). *J Lipid Res.* 41(10): 1658-1665.
Ding, L., A. Derdowski, et al. (2003). *J Virol.* 77(3): 1916-1926.
El-Sadr, W. M., C. M. Mullin, et al. (2005). *HIV Med.* 6(2): 114-121.
Empig, C. J. and M. A. Goldsmith (2002). *J Virol.* 76(10): 5266-5270.
Feng, B. and I. Tabas (2002). *J Biol Chem.* 277(45): 43271-43280.
Giguere, J.-F. and M. J. Tremblay (2004). *J Virol.* 78(21): 12062-12065.
Goldstein, J. L. and M. S. Brown (1990). *Nature* 343(6257): 425-430.
Graf, G. A., P. M. Connell, et al. (1999). *J Biol Chem.* 274 (17): 12043-12048.
Graham, D. R. M., E. Chertova, et al. (2003). *J Virol.* 77(15): 8237-8248.
Guyader, M., E. Kiyokawa, et al. (2002). *J Virol.* 76(20): 10356-10364.
Hajjar, D. P. and M. E. Haberland (1997). *J Biol Chem.* 272(37): 22975-22978.
Holm, K., K. Weclewicz, et al. (2003). *J Virol.* 77(8): 4805-4817.
Hsue, P. Y., J. C. Lo, et al. (2004). *Circulation* 109(13): 1603-1608.
Hsue, P. Y. and D. D. Waters (2005). *Circulation* 112(25): 3947-3957.
Itzhaki, R. F. and M. A. Wozniak (2006). *Prog Lipid Res.* 45(1): 73-90.
Jain, M. K. and P. M. Ridker (2005). *Nat Rev Drug Discov* 4(12): 977-987.
Kapadia, S. B., H. Barth, et al. (2007). *J Virol.* 81(1): 374-383.
Katzman, R. B. and R. Longnecker (2003). *J Gen Virol.* 84(11): 2987-2992.
Kaur, T., P. Gopalakrishna, et al. (2004). *Mol Cell Biochem.* 265(1-2): 85-95.
Lavillette, D., B. Bartosch, et al. (2006). *J Biol Chem.* 281(7): 3909-3917.
Leser, G. P. and R. A. Lamb (2005). *Virology* 342(2): 215-227.
Lusis, A. J. (2000). *Nature* 407(6801): 233-241.
Mañes, S., G. del Real, et al. (2000). *EMBO Rep.* 1(2): 190-196.
Manie, S, N., S. Debreyne, et al. (2000). *J Virol.* 74(1): 305-311.
Nguyen, D. H., B. Giri, et al. (2005). *Exp Cell Res.* 304(2): 559-569.
Nguyen, D. H. and J. E. K. Hildreth (2000). *J Virol.* 74(7): 3264-3272.
Nishibori, M., H. K. Takahashi, et al. (2003). *J Pharmacol Sci.* 92(1): 7-12.
Ono, A. and E. O. Freed (2001). *Proc Natl Acad Sci USA.* 98(24): 13925-13930.
Oram, J. F. (2000). *Biochim Biophys Acta.* 1529(1-3): 321-330.
Percherancier, Y., B. Lagane, et al. (2003). *J Biol Chem.* 278(5): 3153-3161.
Popik, W. and T. M. Alce (2004). *J Biol Chem.* 279(1): 704-712.
Reyes-del Valle, J., S. Chavez-Salinas, et al. (2005). *J Virol.* 79(8): 4557-4567.
Rhainds, D., P. Bourgeois, et al. (2004). *J Cell Sci* 117(15): 3095-3105.

Scheiffele, P., A. Rietveld, et al. (1999). *J Biol Chem.* 274(4): 2038-2044.
Soldaini, E., A. Wack, et al. (2003). *Eur J Immunol.* 33(2): 455-464.
Steinberg, D., S. Parthasarathy, et al. (1989). *N Engl J Med.* 320(14): 915-924.
Sun, X. and G. R. Whittaker (2003). *J Virol.* 77(23): 12543-12551.
Tabas, I. (2002). *J Clin Invest.* 110: 583-590.
Tabas, I. (2002). *J Clin Invest.* 110: 905-911.
Takeda, M., G. P. Leser, et al. (2003). *Proc Natl Acad Sci USA.* 100: 14610-14617.
van Wijk, J. P. H., E. J. P. de Koning, et al. (2006). *J Am Coll Cardiol.* 47(6): 1117-1123.
Viard, M., I. Parolini, et al. (2002). *J Virol.* 76(22): 11584-11595.
Vincent, S., D. Gerlier, et al. (2000). *J Virol.* 74(21): 9911-9915.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention. All of the publications, patent applications and patents cited in this specification are incorporated herein by reference in their entirety.

What is claimed is:

1. A method of reducing a cellular cholesterol level, comprising
administering to a subject in need thereof a composition comprising a lipid particle that is capable of cellular entry, wherein the lipid particle comprises 22:6 PE lipid, 22:6 PC lipid, PI lipid and PS lipid.

2. The method of claim 1, wherein the subject comprises at least one cell and wherein, prior to said administering, the at least cell comprises at least one cell infected with a virus and wherein said administering reduces an infecting ability of the infected cell.

3. The method of claim 2, wherein the virus is an HCV virus.

4. The method of claim 1, wherein the subject is a warm-blooded animal.

5. The method of claim 4, wherein the subject is a human being.

6. The method of claim 5, wherein said administering results in at least one of treating or preventing a disease or condition, that is caused by or associated with an increased cellular cholesterol level.

7. The method of claim 6, wherein the disease or condition is atherosclerosis or coronary artery disease.

8. The method of claim 7, wherein the subject is a subject infected with an immunodeficiency virus and wherein the atherosclerosis or coronary disease are caused by or associated with an immunodeficiency virus.

9. The method of claim 4, wherein said administering results in treating or preventing a disease or condition, that is caused by or associated with a virus, that depends on intracellular cholesterol for replication.

10. The method of claim 9, wherein the virus is selected from herpes simplex virus, influenza virus, murine leukemia virus, vaccinia virus, polyoma virus, Epstein-Barr virus, Semiliki Forest virus, Ebola virus, Marburg virus, dengue virus, measles virus, HIV, hepatitis C virus and hepatitis B virus.

11. The method of claim 9, wherein the composition further comprises an antiviral agent encapsulated inside the lipid particle.

12. The method of claim 4, wherein the administering is performed subcutaneously.

13. The method of claim 1, wherein the lipid particle is a liposome.

14. The method of claim 1, wherein said administering reduces a cellular level of esterified cholesterol.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctcccggggc actcgcaagc                                                 20

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgccatggc gttagta                                                    17